(12) United States Patent
Shaw

(10) Patent No.: US 9,468,510 B2
(45) Date of Patent: *Oct. 18, 2016

(54) FLOSS DEVICE, A METHOD OF FORMING THE FLOSS DEVICE AND A METHOD OF USING THE FLOSS DEVICE

(71) Applicant: Richard J. Shaw, Hartland, WI (US)

(72) Inventor: Richard J. Shaw, Hartland, WI (US)

(73) Assignee: Richard J. Shaw, Hartland, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/339,845

(22) Filed: Jul. 24, 2014

(65) Prior Publication Data

US 2014/0335474 A1 Nov. 13, 2014

Related U.S. Application Data

(63) Continuation-in-part of application No. 13/865,276, filed on Apr. 18, 2013, now abandoned, which is a continuation-in-part of application No. 12/077,916, filed on Mar. 24, 2008, now Pat. No. 8,541,047.

(51) Int. Cl.
*A61C 15/04* (2006.01)
*A01N 25/02* (2006.01)
*A61C 3/00* (2006.01)
*A61C 15/02* (2006.01)

(52) U.S. Cl.
CPC ..................................... *A61C 15/02* (2013.01)

(58) Field of Classification Search
None
See application file for complete search history.

(56) References Cited

U.S. PATENT DOCUMENTS

| 1,451,380 | A | | 4/1923 | Rudolf |
| 3,101,727 | A | | 8/1963 | Wiseman |
| 3,672,378 | A | | 6/1972 | Silverman |
| 3,674,901 | A | | 7/1972 | Shepherd et al. |
| D308,265 | S | * | 5/1990 | Shaw et al. ................. D28/65 |
| 5,002,769 | A | | 3/1991 | Friedman |
| 5,178,537 | A | * | 1/1993 | Currie ............................ 433/72 |
| 5,503,842 | A | | 4/1996 | Fazan et al. |
| 5,875,798 | A | | 3/1999 | Petrus |
| 6,220,258 | B1 | * | 4/2001 | Briggs et al. ................ 132/329 |

(Continued)

FOREIGN PATENT DOCUMENTS

| WO | 0145583 | 6/2001 |
| WO | 2008068400 | 6/2008 |
| WO | 2012030203 | 8/2012 |

OTHER PUBLICATIONS

Perkinelmer, Inc., Nylon 6—Influence of Water on Mechanical Properties and Tg, Application Note, Thermal Analysis, 2007, 2 pages.

*Primary Examiner* — Jeffrey T Palenik
(74) *Attorney, Agent, or Firm* — Thomas J. Connelly; Northwind IP Law, S.C.

(57) ABSTRACT

A floss device is disclosed which is designed to be used to floss between adjacent teeth in a person's mouth. The floss device includes a first portion joined to a second portion. The first portion has an arcuate configuration which terminates in a rounded tip. The second portion is linear and terminates in an enlarged distal end which is designed to be grasped between a person's thumb and index finger and facilitates manipulation of said floss device. The floss device also has a textured outer surface that can temporarily retain a solution or liquid medication and then transfer the solution or liquid medication onto the teeth and surrounding soft tissue in a person's mouth. A method of molding the floss device and a method of using the floss device are also disclosed.

21 Claims, 9 Drawing Sheets

(56) References Cited

U.S. PATENT DOCUMENTS

| | | |
|---|---|---|
| 2002/0117184 A1 | 8/2002 | Kragh |
| 2003/0134255 A1 | 7/2003 | Masterman |
| 2005/0058609 A1 | 3/2005 | Nazeri |
| 2006/0070195 A1 | 4/2006 | Morita et al. |
| 2006/0243409 A1* | 11/2006 | Fish et al. .................... 162/329 |
| 2011/0099735 A1 | 5/2011 | Stadeker |
| 2013/0037046 A1 | 2/2013 | Loera Pulido |

\* cited by examiner

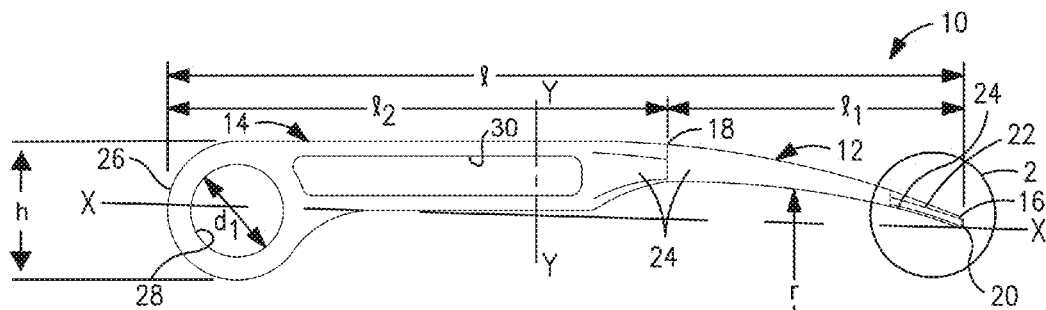
FIG. 1
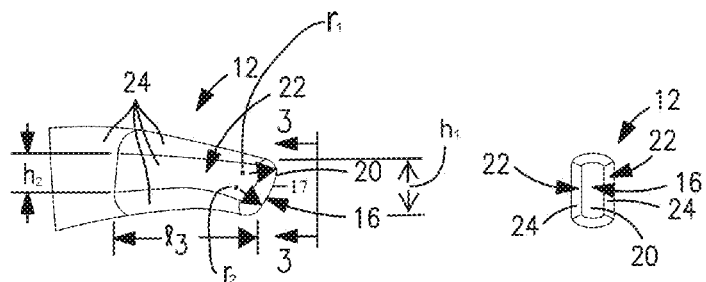 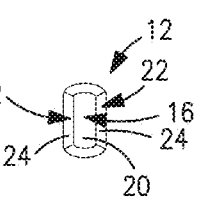
FIG. 2  FIG. 3
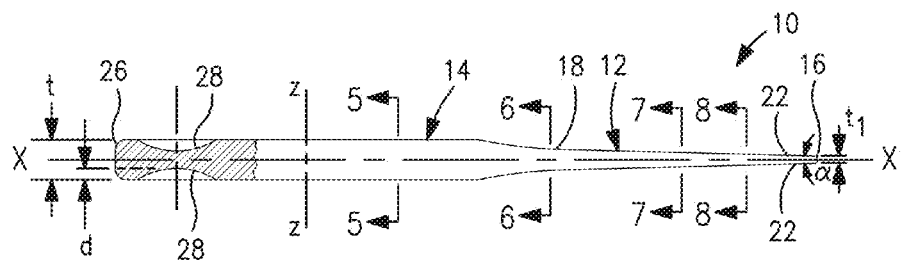
FIG. 4
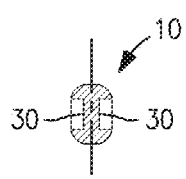 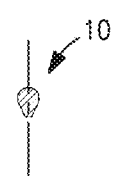  
FIG. 5  FIG. 6  FIG. 7  FIG. 8

A method of forming a floss device having an arcuately shaped first portion terminating in a rounded tip and a second portion secured to said first portion opposite said rounded tip, and said floss device capable of being used to probe between a person's teeth, said method comprising the steps of:

introducing a moldable plastic resin into a mold cavity and molding a floss device;

allowing said floss device to solidify;

removing said solidified floss device from said mold cavity; and immediately immersing said solidified floss device in a solution or a liquid medication for a sufficient time so that said textured outer surface can absorb a predetermined amount of said solution or liquid medication.

FIG. 9

A method of using a floss device having an arcuately shaped first portion terminating in a rounded tip and a second portion secured to said first portion opposite said rounded tip, and said floss device capable of being used to probe between a person's teeth and delivering an antimicrobial solution to said teeth and surrounding soft tissue of the person's mouth, said method comprising the steps of:

manipulating said rounded tip around and between a first of two adjacent teeth to remove any foreign objects lodged therebetween and allowing said pair of sides to breakup plaque and tartar present on said teeth;

repositioning said floss device and manipulating said rounded tip around and between a second of two adjacent teeth to remove any foreign objects lodged therebetween and allowing said pair of sides to breakup plaque and tartar present on said teeth; and repositioning said floss device and manipulating said rounded tip around and between additional pairs of teeth to remove any foreign objects lodged therebetween and allowing said pair of sides to breakup plaque and tartar present on said teeth.

FIG. 10

FLOSS DEVICE, A METHOD OF FORMING THE FLOSS DEVICE AND A METHOD OF USING THE FLOSS DEVICE

CROSS REFERENCE TO RELATED APPLICATIONS

This application is a Continuation-In-Part of U.S. Ser. No. 13/865,276, filed Apr. 18, 2013, entitled: A FLOSS DEVICE, A METHOD OF FORMING THE PROBE AND A METHOD OF USING THE PROBE, which is a Continuation-In-Part of U.S. Ser. No. 12/077,916, filed Mar. 24, 2008, entitled: POLAR ANTISEPTIC/ANTIBACTERIAL CONTAINING TOOTHPICK PROBES, now U.S. Pat. No. 8,541,047, granted Sep. 24, 2013.

FIELD OF THE INVENTION

This invention relates to a floss device, a method of forming the floss device and a method of using the floss device.

BACKGROUND OF THE INVENTION

String floss is the most common oral flossing device used today. Nearly every dental professional considers flossing to be an important part of oral hygiene which compliments brushing. However, the shortcomings associated with string floss causes many people not to floss.

The regions between a person's teeth and gums can serve as reservoirs of infection with diseased gums and buildup of plaque and tarter. Bad breath is a common side effect. Flossing should massage the gum while removing the buildup of diseased plaque and/or tartar from the interperoximal regions of the teeth. Massaging the gum is an important function of string flossing. Flossing stimulates blood circulation near the surface of the tissue. The mechanical removal of plaque and/or tartar is an added benefit.

One of the drawbacks with string floss is that a user must wrap the string floss around his/her index finger on both hands. This requires a certain amount of dexterity which some people, especially the elderly, may not have. The string floss usually encircled each of the index fingers by two or more revolutions. As the person moves their hands apart to draw the string floss tight, the string floss actually starts to cut into their fingers. This can cause irritation and is uncomfortable. A second drawback with using string floss is that when it gets wet, it becomes slippery and a person may have a hard time trying to hold it between his/her index finger on each hand. A third drawback is that string floss tends to break when moved between two adjacent teeth that are tightly aligned. The person trying to floss is then required to get a new length of string floss. Also, sometimes, a portion of the broken string floss can become lodged between the two tightly aligned teeth and it is difficult to remove the broken section. A fourth drawback is that it is sometimes difficult for the string floss to gain access to the interperoximal regions of the teeth. Tightly aligned teeth can acerbate this problem. Manufacturers have reduced the diameter of string floss and have also coated string floss with wax, TEFLON and other substances in an attempt to facilitate getting the string floss to slide between tightly aligned teeth. However, the inherent problems with string floss still persist.

In addition to the above-identified problems with using string floss, it is well known that string floss does not effectively breakup plaque and/or tartar. The strength required for string floss to move between adjacent teeth leaves only longitudinal filament fabrication as a suitable option. Any braiding or texturing of the string floss results in a loss of strength or increases its diameter. Because of this, string floss cannot be fabricated with the ability to mechanically breakup plaque and/or tartar.

Furthermore, people have tried to modify string floss so as to provide medication while flossing. However, no successful products have ever been commercialized.

String floss is often used by people to remove food and debris trapped between adjacent teeth because a toothpick is incapable of probing into these inaccessible areas. The string floss can force the food and debris into the interperoximal regions of the teeth where it lodges. This can exacerbate an infectious condition because the food and debris can develop into another source of infection.

Still another drawback with string floss can occur in a dental office. Many dental hygienists have been accidentally bitten by a patient when they try to floss the patients teeth.

A further disadvantage of string floss is that it cannot be used by a person wearing braces.

Lastly, periodontal disease, tooth decay and other serious health issues, such as heart attacks, can be attributed to unhealthy gums. Surgical procedures are often delayed until gum diseases are brought under control because the diseased gums can contribute or develop into other medical problems. Other serious health maladies are attributed to diseased gums. In fact, the U.S. military has recognized the problems associated with exacerbated gum disease.

Now a floss device, a method of forming the floss device and a method of using the floss device have been invented which overcomes the above mentioned problems and issues. This floss device is designed to be used by the general public as well as by dentists and dental hygienists.

SUMMARY OF THE INVENTION

Briefly, this invention relates to a floss device, a method of forming the floss device and a method of using the floss device. A floss device includes a length measured along a longitudinal central axis, a height measured along a vertical central axis and a thickness measured along a transverse central axis. The floss device has a first portion joined to a second portion along its length. The first portion has an arcuate configuration which curves along the vertical central axis and tapers inward along the transverse central axis to a narrow dimension and terminates in a rounded tip. The rounded tip has a height which includes a first radius, a spaced apart second radius and a rounded surface therebetween. The second portion is linear and terminates in an enlarged distal end which is designed to be grasped between a person's thumb and index finger. The enlarged distal end has a pair of oppositely aligned indentations formed therein. The enlarged distal end is aligned parallel to the height of the rounded tip. The enlarged distal end and its pair of indentations facilitate manipulation of the floss device by a person to probe around and between a person's teeth. The floss device also has a textured outer surface which extends rearward from the rounded tip over at least a portion of the floss device. The textured outer surface has a micro-contoured profile which increases surface tension and facilitates the retention of a greater quantity of a solution or medication. The textured outer surface also facilitates mechanical breakup of plaque and tartar.

A method of forming a floss device, having the features described above, is also disclosed. The method includes the steps of introducing a moldable plastic resin into a mold cavity and molding a floss device. The molded floss device is then allowed to solidify. The solidified floss device is then removed from the mold cavity. The floss device is then immediately immersed in a solution or a liquid medication for a sufficient time so that the textured outer surface can absorb a predetermined amount of the solution or liquid medication.

A method of using a floss device having a length measured along a longitudinal central axis, a height measured along a vertical central axis and a thickness measured along a transverse central axis. The floss device has a first portion joined to a second portion along its length. The first portion has an arcuate configuration which curves along the vertical central axis and tapers inward along the transverse central axis to a narrow dimension and terminates in a rounded tip. The rounded tip has a height which includes a first radius, a spaced apart second radius and a rounded surface therebetween. A portion of the first portion has a pair of oppositely aligned sides extending along the longitudinal central axis. The pair of sides taper inward towards one another and terminate approximate the rounded tip. The pair of sides is aligned parallel to the vertical central axis. The second portion is linear and terminates in an enlarged distal end which is designed to be grasped between a person's thumb and index finger. The enlarged distal end has a pair of oppositely aligned indentations formed therein. The enlarged distal end is aligned parallel to the height of the rounded tip. The enlarged distal end, with the pair of indentations, facilitates manipulation of the floss device by a person to probe around and between a person's teeth. The floss device also has a textured outer surface which extends rearward from the rounded tip over at least a portion thereof. The textured outer surface has a micro-contoured profile which increases surface area and surface tension, and facilitates the retention of a greater quantity of a solution or medication. The method comprising the steps of manipulating the rounded tip around and between a first of two adjacent teeth to remove any foreign objects lodged therebetween and allowing the pair of sides to breakup plaque and/or tartar present on the teeth. The method also includes repositioning the floss device and manipulating the rounded tip around and between a second of two adjacent teeth to remove any foreign objects lodged therebetween and allowing the pair of sides to breakup plaque and/or tartar present on the teeth. The method further includes repositioning the floss device and manipulating the rounded tip around and between additional pairs of teeth to remove any foreign objects lodged therebetween and allowing the pair of sides to breakup plaque and/or tartar present on the teeth.

The general object of this invention is to provide a floss device having a textured outer surface which is capable of temporarily absorbing a solution or medication and later releasing the solution or medication onto the teeth and surrounding soft tissue in a person's mouth. A more specific object of this invention is to provide a floss device which can mechanically remove foreign objects trapped between a person's teeth, as well as delivering an antimicrobial solution or a medication onto the teeth and surrounding soft tissue in a person's mouth.

Another object of this invention is to provide a floss device having a unique geometry which includes a rounded tip to be used to caress and massage the soft tissue of a person's mouth.

A further object of this invention is to provide a method of forming the floss device.

Still further, an object of this invention is to provide method of using the floss device.

Other objects and advantages of the present invention will become more apparent to those skilled in the art in view of the following description and the accompanying drawings.

BRIEF DESCRIPTION OF THE DRAWINGS

FIG. 1 is a side view of the floss device of this invention.
FIG. 2 is an enlarged view of the rounded tip of the floss device shown in FIG. 1.
FIG. 3 is an end view of the rounded tip shown in FIG. 2.
FIG. 4 is a top view of the floss device shown in FIG. 1.
FIG. 5 is a cross-sectional view taken along line 5-5 of FIG. 4.
FIG. 6 is a cross-sectional view taken along line 6-6 of FIG. 4.
FIG. 7 is a cross-sectional view taken along line 7-7 of FIG. 4.
FIG. 8 is a cross-sectional view taken along line 8-8 of FIG. 4.
FIG. 9 is a flow diagram depicting a method of forming a floss device.
FIG. 10 is a flow diagram depicting a method of using a floss device.

DETAILED DESCRIPTION OF THE INVENTION

Figure 11:
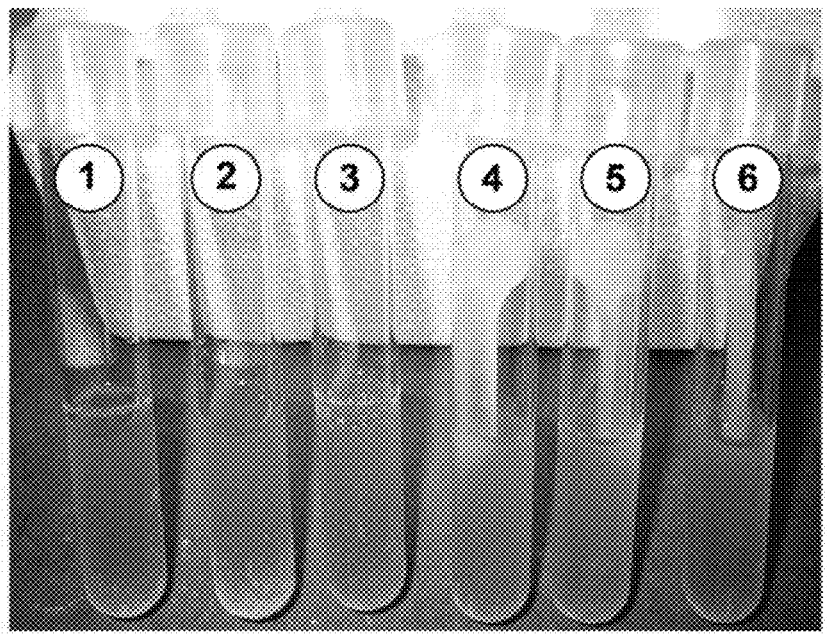
FIG. 11 is a photograph of six test tubes.

Referring to FIG. 1, a floss device 10 is shown which has a textured outer surface which is capable of absorbing and later releasing a solution or medication onto the teeth and surrounding soft tissue of a person's mouth. The floss device 10 is designed to be used by the general public, by dentists, by dental hygienists or by a caregiver. The floss device 10 can be used with or without a solution or a medication. The solution can be an antimicrobial, an antiseptic, an antibacterial, a combination antiseptic and antibacterial, or some other form of solution. The medication can be any medication known to man which can treat an existing problem in the mouth. Desirably, the medication is in liquid form which is capable of being absorbed into the floss device 10. Alternatively, the medication can be a paste or a semi-solid which is smeared onto or carried on the outer surface of the floss device 10 and can be rubbed off by contact with the teeth and/or surrounding soft tissue of a person's mouth. The floss device 10 can function as a massaging and caressing probe for oral hygiene. The floss device 10 can be utilized by a human or be used on an animal. A person could use the floss device 10 to probe around and between his or her teeth. Alternatively, a dentist, dental hygienist or a caregiver could use the floss device on a patient, on a young child, on an older adult or on an incapacitated person. Likewise, a veterinarian, a pet owner, a farmer or an animal handler could use the floss device 10 on one or more animals, such as on dogs, cats, farm animals, etc.

Referring now to FIGS. 1-4, the floss device 10 has a longitudinal central axis X-X, a vertical central axis Y-Y, and a transverse central axis Z-Z, see FIG. 4. The floss device 10 has a length l measured along the longitudinal central axis X-X, a height h measured along the vertical central axis Y-Y, and a thickness t measured along the transverse central axis Z-Z. The floss device 10 includes a first portion 12 joined to a second portion 14 along its length l. In other words, the first and second portions, 12 and 14 share the same longitudinal central axis X-X. The thickness t of the floss device 10 is non-uniform along s length l.

The first portion 12 can vary in size, shape and configuration. The first portion 12 is a slender, flexible member used to explore around and between a person's teeth. The first portion 12 can also be used to massage or caress the soft tissue of a person's mouth located adjacent to or between the teeth. The first portion 12 is arcuately shaped. By "arcuate" it is meant a shape in the form of a bow or curve. The arcuately shaped first portion 12 can be formed on a radius r which can vary in dimension. Desirably, the radius r is between about 0.3 inches to about 0.7 inches. More desirably, the radius r is between about 0.4 inches to about 0.6 inches. Even more desirably, the radius r is between about 0.4 inches to about 0.5 inches. Most desirably, the radius r is about 0.45 inches. As stated above, the first portion 12 is flexible. By "flexible" it is meant that it is capable of being bent or flexed; pliable. The first portion 12 can also be resilient. By "resilient" it is meant that the material forming the first portion 12 possesses a property that enables it to resume its original shape or position after being bent, stretched, or compressed; elasticity.

The first portion 12 curves along the vertical central axis Y-Y and tapers inward along the transverse central axis Z-Z to a narrow dimension and terminates in a rounded tip 16.

The second portion 14 can also vary in size shape and configuration. The second portion 14 functions as a handle or gripping portion which allows a person to comfortably hold and manipulate the floss device 10. The second portion 14 is shown as being linear. However, the second portion 14 could be formed in various other shapes, if desired. For example, the second portion 14 could contain a bend or offset to facilitate its use. The second portion 14 does not need to be as flexible as the first portion 12. Therefore, the second portion 14 can be rigid, semi-rigid or be less susceptible to bending or flexing than the first portion 12. Alternatively, the second portion 14 can be constructed to be as flexible as the first portion 12, if desired.

The first portion 12 and the second portion 14 are generally formed from the same material. The first and second portions, 12 and 14 respectively, can be molded simultaneously in a single mold to form an integral floss device 10. Alternatively, the second portion 14 could be formed from a different material than the first portion 12. In addition, the first portion 12 could be molded and the second portion 14 could be connected, joined or somehow attached to the first portion 12.

Referring again to FIG. 1, the floss device 10 has an overall length l. The length l of the floss device 10 can vary in dimension. Desirably, the length l of the floss device 10 is less than about 4 inches. More desirably, the length l of the floss device 10 is less than about 3 inches. Even more desirably, the length l of the floss device 10 is less than about 2.5 inches. Most desirably, the length l of the floss device 10 is about 2.25 inches.

The first portion 12 of the floss device 10 has a length $l_1$ and the second portion 14 of the floss device 10 has a length $l_2$. The length $l_1$ of the first portion 12 can be greater than, equal to or be less than the length $l_2$ of the second portion 14. Desirably, the length $l_1$ of the first portion 12 is equal to or less than the length $l_2$ of the second portion 14. More desirably, the length l of the first portion 12 is less than the length $l_2$ of the second portion 14. The length $l_1$ of the first portion 12 can range from about 0.4 inches to about 1 inch. Desirably, the length $l_3$ of the first portion 12 is at least about 0.6 inches. More desirably, the length l of the first portion 12 is at least about 0.75 inches. Even more desirably, the length $l_1$ of the first portion 12 is about 0.8 inches. The length $l_2$ of the second portion 14 can range from about 0.4 inches to about 1.5 inch. Desirably, the length $l_2$ of the second portion 14 is at least about 0.8 inches. More desirably, the length $l_2$ of the second portion 14 is about 1 inch. Even more desirably, the length $l_2$ of the second portion 14 is greater than about 1 inch. Most desirably, the length $l_2$ of the second portion 14 is about 1.15 inches.

Referring again to FIGS. 1 and 4, the first and second portions, 12 and 14 respectively, create an integral member. By "integral" it is meant a complete unit. The first and second portions, 12 and 14 respectively, extend axially along the longitudinal central axis X-X. Alternatively, at least a portion of the first and second portions, 12 and 14 respectively, can extend axially along the longitudinal central axis X-X. If desired, at least a portion of the second portion 14 can be formed at an angle, or be bent relative to the first portion 12.

It should also be noted that the arcuately shaped first portion 12 curves downward along the vertical central axis Y-Y. This curvature facilitates easy use of the floss device 10. This curvature also permits the floss device 10 to be inserted around a tooth or between adjacent teeth in a comfortable manner.

Referring to FIG. 4, the second portion 14 of the floss device 10 has a thickness which can vary in dimension along at least a portion of its length $l_2$. The maximum thickness t of the floss device 10 occurs in the second portion 14. The thickness of the second portion 14 can be constant or can vary. Usually, the thickness of the second portion 14 will vary along its length $l_2$.

In FIG. 4, one will notice that the thickness of the first portion 12 narrows down as it approaches the rounded tip 16. The rounded tip 16 has a thickness $t_1$. The thickness of the first portion 12 is generally less than the thickness of the second portion 14. Typically, the thickness of the second portion 14 is greater than a major portion of the thickness of the first portion 12. In addition, the first portion 12 reduces in thickness as it approaches the rounded tip 16. The maximum thickness of the second portion 14 can range from about 0.1 inches to about 0.25 inches. Desirably, the maximum thickness of the second portion 14 is less than about 0.2 inches. More desirably, the maximum thickness of the second portion 14 is less than about 0.15 inches. Most desirably, the maximum thickness of the second portion 14 is about 0.12 inches.

The maximum thickness of the first portion 12 can be less than about 0.25 inches. Desirably, the maximum thickness of the first portion 12 is less than about 0.2 inches. More desirably, the maximum thickness of the first portion 12 is less than about 0.15 inches. Even more desirably, the maximum thickness of the first portion 12 is less than about 0.1 inches. The minimum thickness of the first portion 12 can vary. The minimum thickness of the first portion 12 can be less than about 0.015 inches.

The floss device 10 can be formed from a variety of materials. The floss device 10, or at least a portion of the floss device 10, should be capable of being formed or molded from one or more materials. Desirably, the floss device 10 is injection molded. For example, the floss device 10 could be injection molded using a two piece mold with a mold cavity, as is well known in the art. Alternatively, the floss device 10 could be formed using other methods known to those skilled in the art. The floss device 10 could be formed from a thermoplastic or plastic material. Nylon is a thermoplastic material from which the floss device 10 can be formed. A particular nylon that is well suited to being molded into the floss device 10 is Nylon 6. By "nylon" it is meant any of a family of high-strength, resilient synthetic polymers containing recurring amide groups. Type 6, 6 Nylon 101 is the most common commercial grade of nylon, and Nylon 6 is the most common commercial grade of molded nylon. The floss device 10 could also be formed from other polymers and/or copolymers. Such polymers and/or copolymers could have similar characteristics as Nylon 6. By "polymer" it is meant any of numerous natural or synthetic compounds of usually high molecular weight consisting of repeated linked units, each a relatively light and simple molecule. By "copolymer" it is meant a polymer of two or more different monomers.

Nylons are condensation copolymers formed by reacting equal parts of a diamine and a dicarboxylic acid, so that amides are formed at both ends of each monomer in a process analogous to polypeptide biopolymers. Chemical elements included are carbon, hydrogen, nitrogen and oxygen. The numerical suffix specifies the number of carbons donated by the monomers: the diamine first and the diacid second. The most common variant is nylon 6, 6 which refers to the fact that the diamine (hexamethylene diamine, IUPAC name: hexane-1,6 diamine) and the diacid (adipic acid, IUPAC name: hexanedioic acid) each donate 6 carbons to the polymer chain. As with other regular copolymers like polyesters and polyurethanes, the "repeating unit" consists of one of each monomer, so that they alternate in the chain. Since each monomer in this copolymer has the same reactive group on both ends, the direction of the amide bond reverses between each monomer, unlike natural polyamide proteins which have overall directionality: C terminal→N terminal. In the laboratory, nylon 6, 6 can also be made using adipoyl chloride instead of adipic.

E. I. du Pont de Nemours and Company, having an office at 1007 Market Street, Wilmington, Del. 19898 patented nylon 6, 6. In order to compete with E. I. du Pont de Nemours and Company, other companies, particularly the German company, BASF, developed the homopolymer Nylon 6, or polycaprolactam which is not a condensation polymer, but formed by a ring-opening polymerization (alternatively made by polymerizing aminocaproic acid). The peptide bond within the caprolactam is broken with the exposed active groups on each side being incorporated into two new bonds as the monomer becomes part of the polymer backbone. In this case, all amide bonds lie in the same direction, but the properties of Nylon 6 are sometimes indistinguishable from those of nylon 6, 6, except for melt temperature and some fiber properties in products like carpets and textiles. There is also Nylon 9.

The 428° F. (220° C.) melting point of Nylon 6 is lower than the 509° F. (265° C.) melting point of nylon 6, 6.

Referring to FIG. 2, one will clearly see that the first portion 12 terminates in a rounded tip 16. By a "rounded tip" it is meant a dull end, not sharp. The rounded tip 16 is not a pointed tip. The rounded tip 16 has a height $h_1$ which includes a first radius a spaced apart second radius $r_2$, and a rounded surface 17. The first radius $r_1$ can be equal to the second radius $r_2$. Alternatively, the first radius $r_1$ can be different from the second radius $r_2$. The first and second radiuses, $r_1$ and $r_2$ respectively, can be equal or vary in dimension. The first radius $r_1$ can range from between about 0.1 to about 0.3 inches. Desirably, the first radius r can range from between about 0.1 to about 0.2 inches. More desirably, the first radius $r_1$ is about 0.015 inches. The second radius $r_2$ can range from between about 0.1 to about 0.3 inches. Desirably, the second radius $r_2$ can range from between about 0.1 to about 0.2 inches. More desirably, the second radius $r_2$ is about 0.015 inches.

Still referring to FIG. 2, the rounded surface 17 can vary in configuration. The rounded surface 17 can be a portion of a circular arc or have a semi-circular shape. The rounded surface 17 does not contain any sharp or pointed edges or points. Instead, the rounded surface 17 is smooth and is free of irregularities, roughness or projections.

Referring now to FIG. 4, the second portion 14 is secured to the first portion 12 at a location opposite to the rounded tip 16. The surface or line of securement between the first and second portions, 12 and 14 respectively, is designated 18. The first portion 12 narrows or tapers down along the transverse central axis Z-Z from the surface or line of securement 18 to the rounded tip 16. This tapering can be gradual and consistence. Alternatively, the tapering can occur in an irregular or stepped fashion. The rounded tip 16 has a thickness $t_1$ which is less than a majority of the remainder of the floss device 10. The thickness $t_1$ of the rounded tip 16 is less than about 0.015 inches. This narrow dimension facilitates inserting and probing the rounded tip 16 of the floss device 10 around a single tooth or between two adjacent teeth in a person's mouth. The rounded tip 16 can also be used to caress and massage the surrounding soft tissue of a person's mouth. The surrounding soft tissue is located adjacent to or between the person's teeth. The floss device 10 can also be constructed to deliver a solution, such as an antimicrobial solution, an antiseptic, an antibacterial, a combination antiseptic and antibacterial, or some other form of a medication to the teeth and the surrounding soft tissue of a person's mouth. More discussion about this added feature will be explained shortly.

Still referring to FIG. 4, it should be understood that when the floss device 10 is viewed from above, the rounded tip 16 is curved and smooth along the transverse central axis Z-Z. The rounded tip 16 is depicted as having a semi-circular configuration. In other words, when viewed from the top, the rounded surface 16 is not a sharp point.

Still again to FIG. 2, the side profile of the rounded tip 16 shows the first radius $r_1$, the second radius $r_2$ and a rounded surface 17 located therebetween. The rounded surface 17 is smooth. The rounded surface 17 creates an end 20 which represents the forward end of the floss device 10. The rounded surface 17 can be a portion of a circular arc. Alternatively, the rounded surface 17 can have a semi-circular shape. The smooth, rounded surface 17 does not have any sharp edges. The presence of the smooth, rounded surface 17 assures that the soft tissue of a person's mouth will not be cut or impaled by maneuvering and probing the floss device 10 around and between the various teeth in a person's mouth.

The rounded tip 16 has a height $h_1$ which can vary in dimension. The height $h_1$ of the rounded tip 16 is aligned parallel to the vertical central axis Y-Y. The height $h_1$ of the rounded tip 16 can be less than about 0.1 inches.

Still referring to FIGS. 2 and 4, the first portion 12 of the floss device 10 also Includes a pair of sides 22, 22. The pair of sides 22, 22 can be oppositely aligned to one another. The pair of sides 22, 22 diverge away from the end 20. In other words, the pair of sides 22, 22 are aligned closest together approximate the rounded tip 16. The pair of sides 22, 22 angle or taper backward toward the remainder of the first portion 12. Desirably, the pair of sides 22, 22 taper rearward away from the rounded tip 16. The pair of sides 22, 22 can be aligned parallel to the vertical central axis Y-Y or be formed at an angle thereto. Desirably, the pair of sides 22, 22 is aligned parallel to the vertical central axis Y-Y. The pair of sides 22, 22 can taper away from the rounded tip 16 at any desired angle alpha ($\alpha$), see FIG. 4. The angle of taper $\alpha$ can range from between about 2 degrees to about 45 degrees. Desirably, the angle of taper $\alpha$ can range from between about 5 degrees to about 30 degrees. More desirably, the angle of taper $\alpha$ can range from between about 7 degrees to about 25 degrees. Most desirably, the angle of taper $\alpha$ is less than about 20 degrees.

Referring again to FIG. 2, the dimensions of the pair of sides 22, 22 can vary. Each of the pair of sides 22, 22 has a length $l_3$ measured along the longitudinal central axis X-X and a height $h_2$ measured parallel to the vertical central axis Y-Y. The length $l_3$ of each of the pair of sides 22, 22 is less than about 0.3 inches, Desirably, the length $l_3$ of each of said pair of sides 22, 22 is less than about 0.25 inches. More desirably, the length $l_3$ of each of the pair of sides 22, 22 is about 0.2 inches. The height $h_2$ of each of the pair of sides 22, 22 is less than about 0.03 inches. Desirably, the height $h_2$ of each of the pair of sides 22, 22 is less than about 0.02 inches. More desirably, the height $h_2$ of each of the pair of sides 22, 22 is about 0.015 inches.

The pair of sides 22, 22 function to breakup plaque and/or tartar on a person's teeth. The surface area of each of the pair of sides 22, 22 is sufficiently large to accomplish this task.

Still referring to FIG. 2, the floss device 10 also has a textured outer surface 24. The textured outer surface 24 extends rearward from the rounded tip 16. The textured outer surface 24 can cover the entire floss device 10. Alternatively, the textured outer surface 24 can be formed only on a portion of the floss device 10. Another option is to form the textured outer surface on only the first portion 12. A further option is to form the textured outer surface 24 on only a portion of the first portion 12.

The textured outer surface 24 can extend over the entire length 1 of the floss device 10. This means that the entire length $l_1$ of the first portion 12 and the entire length $l_2$ of the second portion 14 are covered by the textured outer surface 24. Alternatively, the textured outer surface 24 could extend over the length of the first portion 12 and only over a portion of the length $l_2$ of the second portion 14. Still another alternative is that the textured outer surface 24 could extends over the length $l_1$ of the first portion 12 but not over any portion of the length $l_2$ of the second portion 14. Desirably, the textured outer surface 24 extends over at least about 10% of the length 1 of the floss device 10.

The textured outer surface 24 can surround the circumference of the floss device 10. Alternatively, the textured outer surface 24 can surround only a portion of the circumference. Desirably, the textured outer surface 24 surrounds the circumference of the floss device 10. In other words, the textured outer surface 24 surrounds 360 degrees of the floss device 10 and extends over a predetermined length thereof.

The textured outer surface 24 can contain an "Amtex 9105" texture. "Amtex 9105" is a designation of Amtex, a company having an office at W22410 Edgewood Avenue, Big Bend, Wis. 53103. Amtex is in the business of advanced mold texturing. A textured surface is a far variation from a polished or smooth surface. A textured surface has much more surface area because it is a surface made with added detail including micro-pockets, reservoirs, indentations, etc. This micro-contoured profile brings several attributes. The micro-contoured profile increases the surface tension of the floss device 10 and facilitates the retention of a greater quantity of a solution or liquid medication. The textured outer surface 24 is also capable of acting as a scouring surface in that it can mechanically contribute to the breakup of plaque and/or tartar on a tooth as it is moved back and forth relative to a tooth. The textured outer surface 24 is further capable of temporarily retaining a solution or a liquid medication. A smooth surface formed on a plastic member will retain very little, if any, of a solution or liquid medication because the cohesion and surface tension of a smooth plastic surface is near zero. The textured outer surface 24 of the floss device 10 with its micro-contoured profile is able to temporarily retain a solution or a liquid medication and then release this solution or liquid medication onto the teeth and surrounding soft tissues in a person's mouth.

It should be understood that if the medication is in a solid or semi-solid state, for example a paste, the medication can be physically retained on the textured outer surface 24 of the floss device 10 and be transferred to the teeth and/or the surrounding soft tissue by contact therewith.

It should also be understood that no micro-pockets, reservoirs or indentations are actually physically formed into the floss device 10. Instead, the textured outer surface 24 of the floss device 10 contains the micro-contoured profile which can temporarily retain a solution or liquid medication.

It should be further understood that the textured outer surface 24 will extend over each of the pair of sides 22, 22. This means that the pair of sides 22, 22 can deliver a solution or medication as well as be used to breakup plaque and/or tartar on a person's teeth.

The floss device 10 can be used with or without the presence of the solution or medication. In addition, a floss device 10 which has not absorbed a solution or liquid medication can still be used to transport a solution or medication to the teeth and surrounding soft tissue of a person's mouth if it is first dipped, partially submerged or immersed into a solution or liquid medication. By allowing the floss device 10 to absorb a given amount of a solution or medication, this solution or liquid medication can be transported onto the teeth and surrounding soft tissues in a person's mouth. By probing, flexing or maneuvering the floss device 10 in between a person's teeth and caressing or massaging a person's gums and surrounding soft tissue, the solution or medication can be transferred from the floss device 10 to the person's teeth and surrounding soft tissue.

The maximum moisture saturation of a nylon resin is about 2.7%. By dipping or submerging the floss device 10, with its textured outer surface 24, into a solution or into a liquid medication, the volume of solution or liquid medication which will cling or be assimilated onto the textured outer surface 24 of the floss device 10 can exceed 10% by weight of the floss device 10. The textured outer surface 24 allows the solution or liquid medication to be temporarily retained on the floss device 10. By "temporary" it is meant lasting for only a limited time. This solution or liquid medication is not absorbed into the interstices of the resin molecules from which the floss device 10 is molded but instead will saturate the textured outer surface 24. The floss device 10 can then be inserted into a person's mouth and the teeth and surrounding soft tissue can be caressed or massaged by the first portion 12 of the floss device 10 whereby the solution or liquid medication is transferred to the teeth and the surrounding soft tissue. After a single use, the floss device 10 can be discarded.

The textured outer surface 24 allows at least 3 times the amount of solution or liquid medication to be retained on the floss device 10 versus a smooth surface. Desirably, the textured outer surface 24 allows at least 4 times the amount of solution or liquid medication to be retained on the floss device 10 versus a smooth surface. In this scenario, the floss device 10 can be compared to a sponge. The textured outer surface 24 contains micro-pockets which can temporarily retain a solution or liquid medication. Once the floss device 10 is dipped into a solution or liquid medication, the textured outer surface 24 will retain a high percentage of the solution or liquid medication and this solution or liquid medication can then be immediately transferred to the teeth and the surrounding soft tissue of a person's mouth. Upon contact of the first portion 12 of the floss device 10 with a tooth, the solution or liquid medication will be released from the micro-pockets of the textured outer surface 24 and will be immediately transferred to the outer periphery of the tooth. Any mechanically interaction between the first portion 12 of the floss device 10, such as bending, flexing, back and forth movement, etc. can facilitate the transfer of the solution or liquid medication onto the outer periphery of the teeth and the surrounding soft tissue in a person's mouth.

The dipping procedure is beneficial in certain instances where the solution or liquid medication is not entirely compatible with a floss device 10 molded from a nylon resin. For example, fluorine will dissolve nylon and some other resins from which the floss device 10 could be molded, if the fluorine is in contact with the resin for an extended period of time. Fluoride is a binary compound of fluorine with another element. However, if one dipped a floss device 10 into a fluorine solution and the fluorine was then immediately transferred from the textured outer surface 24 to the teeth and the surrounding soft tissue of a person mouth, the fluorine would not degrade the floss device 10. In this scenario, the floss device 10 would be discarded after a single use.

It should be understood that the medication could be a semi-solid, such as a paste. In this instance, the medication (paste) could be applied to the textured outer surface 24 of the floss device 10 by various ways known to those skilled in the art and then be transferred to the teeth and the surrounding soft tissue of a person's mouth by physical contact of the floss device 10 therewith.

From the above discussion, it should be apparent that the floss device 10 can absorb a solution or liquid medication immediately after it is molded and before it is packaged for sale. Alternatively, the floss device 10 could be sold without having absorbed a solution or liquid medication. In this later scenario, the floss device 10 can be used dry, without any solution or liquid medication, or at a later time the floss device 10 can be partially or fully dipped, submerged or immersed into a container of a solution or liquid medication and then be brought into engagement with the teeth and the surrounding soft tissue in a person's mouth.

Returning to FIG. 2, each of the pair of sides 22, 22 also contains the textured outer surface 24. Each of the pair of sides 22, 22 can be rough, harsh or coarse, marked by irregularities, protuberances or ridges; not smooth. Alternatively, the pair of sides 22, 22 could be made to be abrasive or somewhat abrasive. The purpose of the pair of sides 22, 22 is to facilitate breaking up plaque and/or tartar from the outer periphery of each tooth. By "plaque" it is meant a film of mucus and bacteria on a toothed surface. By "tartar" it is meant a hard yellowish deposit on the teeth, consisting of organic secretions and food particles deposited by various salts. The tapered or angular orientation of the pair of sides 22, 22 ensures that a majority of a tooth periphery can be contacted. Physical contact between the pair of sides 22, 22 and the outer periphery of each tooth causes the breaking up the plaque and/or tartar.

Referring again to FIGS. 1 and 4, one will notice that the second portion 14 of the floss device 10 is linear and terminates in an enlarged distal end 26. The enlarged distal end 26 is spaced apart from the surface or line of securement 18 where the first portion 12 joins the second portion 14. The enlarged distal end 26 is an enlarged area compared to the remainder of the floss device 10 when viewed along the vertical central axis Y-Y axis, see FIG. 1. The enlarged distal end 26 is not located between the rounded tip 16 and the opposite end of the second portion 14. Instead, the enlarged distal end 26 is located at the free end of the second portion 14. This is important for it provides maximum leverage for a person using the floss device 10. The enlarged distal end 26 extends parallel to the vertical central axis Y-Y and extends downward in the same direction as the rounded tip 16. By aligning the enlarged distal end 26 parallel to the height $h_1$ of the rounded tip 16 one can facilitate the manipulation of the floss device 10 around and between the teeth and surrounding soft tissue in a person's mouth.

The shape of the enlarged distal end 26 can vary. In FIG. 1, the enlarged distal end 26 is depicted as having a generally circular configuration. The enlarged distal end 26 has a pair of oppositely aligned indentations 28, 28 formed therein. Each of the pair of indentations 28, 28 is depicted as a circle but could have some other geometrical shape, if desired. Each of the pair of indentations 28, 28 has a diameter $d_1$. The diameter $d_1$ of each of the pair of indentations 28, 28 can vary. The diameter $d_1$ of one of the indentations 28 could be different from the diameter $d_1$ of the other indentation 28, if desired, although it is desirable to form both of the indentations 28, 28 to the same dimension. The diameter $d_1$ of each of the pair of indentations 28, 28 can range from between about 0.2 inches to about 0.75 inches. Desirably, the diameter $d_1$ of each of the pair of indentations 28, 28 is less than about 0.5 inches. More desirably, the diameter $d_1$ of each of the pair of indentations 28, 28 is less than about 0.4 inches. Even more desirably, the diameter $d_1$ of each of the pair of indentations 28, 28 is less than about 0.3 inches.

Each of the pair of indentations 28, 28 also has a depth d, measured parallel to the transverse central axis Z-Z axis. Desirably, each of the pair of indentations 28, 28 has the same depth d. Alternatively, the depth d of one indentation 28 could be different from the depth of the other indentation 28, if desired. The depth d of each of the pair of indentations 28, 28 can vary. Generally, the depth d of each of the pair of indentations 28, 28 can range from between about 0.01 inches to about 0.05 inches. Desirably, the depth d of each of the pair of indentations 28, 28 can range from between about 0.02 inches to about 0.04 inches. More desirably, the depth d of each of the pair of indentations 28, 28 is about 0.03 inches.

The size, shape and configuration of the enlarged distal end 26 functions to permit a person to easily and comfortably grasp the floss device 10 between his or her thumb and index finger. The size, shape and configuration of the distal end 26 further allow a person to hold the floss device 10 firmly between his or her thumb and index finger. For example, the inner tip of the thumb and the inner tip of the index finger can easily grip the floss device 10 therebetween. When held in this manner, the floss device 10 can easily be maneuvered about the various teeth and gum tissue in a person's mouth.

Referring now to FIGS. 5-8, various cross-sectional views of the floss device 10 are depicted. In FIG. 5, a cross-sectional view of the second portion 14 is shown taken along sectional line 5-5. This cross-sectional view reveals an approximately rectangular configuration with rounded corners and a pair of side recesses 30, 30 formed therein. Each of the recesses 30, 30 provides a flat surface where a name, model number, icon, symbol, etc. can be displayed. In FIG. 1, the front view of one of the recesses 30 is shown. It should be understood that any name, model number, icon, symbol, etc. could be displayed in each of the recesses 30, 30. Alternatively, no name or identification need be displayed. In this case, one may wish to eliminate the pair of recesses 30, 30.

FIG. 6 is a cross-sectional view taken along sectional line 6-6 at the securement surface or line 18 where the first portion 12 is joined to the second portion 14. A modified, upside down teardrop profile is shown. The widest part of the modified teardrop shape appears on the top.

FIG. 7 is a cross-sectional view of the first portion 12 taken along sectional line 7-7. As the first portion 12 narrows down as it approaches the rounded tip 16, the cross-section of the first portion 12 likewise gets smaller. A modified, upside down teardrop profile is again shown. The widest part of the modified teardrop shape appears on the top. However, the overall surface area of the first portion 12, shown in FIG. 7, is much smaller than that shown in FIG. 6.

FIG. 8 is another cross-sectional view of the first portion 12 taken along sectional line 8-8, which is closer to the rounded tip 16. As the first portion 12 narrows down as it approaches the rounded tip 16, the cross-section of the first portion 12 continues to get smaller. A modified, upside down teardrop profile is again shown. The widest part of the modified teardrop shape appears on the top. However, the overall surface area of the first portion 12 shown in FIG. 8 is much smaller than that shown in FIG. 7.

Referring again to FIG. 1, when the floss device 10 is formed or molded from a moldable material such as a thermoplastic, a plastic, Nylon 6, etc., the material will contain a plurality of resin molecules having interstices formed therebetween. By "interstices" it is meant a space, especially a small or narrow one, between things or parts. The floss device 10, upon being formed or being removed from a mold cavity, can be contacted with a solution or a liquid medication. The solution or liquid medication can be absorbed into the plastic and be held between the interstices of the resin molecules. Desirably, the floss device 10 is fully or partially immersed in a solution or liquid medication for a predetermined period of time so that a predetermined amount by weight of the solution or liquid medication can be absorbed by the floss device 10. The solution or liquid medication can vary in composition and concentration. The solution can be an antimicrobial solution, an antiseptic solution, an antibacterial solution, a combination of an antiseptic and an antibacterial, or any other known solution. By "antimicrobial" it is meant an agent that kills microorganisms or inhibits their growth. Antimicrobial medicines can be grouped according to the microorganisms they act primarily against. For example, antibacterials (commonly known as antibiotics) are used against bacteria, and antifungals are used against fungi. They can also be classed according to their function. Antimicrobials that kill microbes are called microbicidal; those that merely inhibit their growth are called microbiostatics. Disinfectants such as bleach are non-selective antimicrobials. By "antiseptic" it is meant of, or relating to, or producing antisepsis or associated with the use of antiseptics. An antiseptic is capable of preventing infection by inhibiting the growth of microorganisms. Sometimes "antiseptic" is used to mean a substance that inhibits the growth of disease causing microorganisms. By "antibacterial" it is meant an agent that inhibits bacterial growth or kills bacteria. The term is often used synonymously with the term antibiotics.

The liquid medication can be any medication known to the medical profession.

The solution can be identical to or similar to LISTERINE®. LISTERINE® is a registered trademark of Johnson & Johnson Corporation having a mailing address of: One Johnson & Johnson Plaza, New Brunswick, N.J. 0893-7001.

Another way in which the floss device 10 can be produced is to have it actually absorb a solution or a liquid medication immediately upon its removal from a mold. The solution can be any of those taught above. The liquid medication can vary. Any known Federal Drug Administration (FDA) approved medication in liquid form can be absorbed into the floss device 10 provided it does not degrade the plastic resin from which the floss device 10 is molded. The liquid medication can be transferred to the soft tissue, such as the gums, of the person as the floss device 10 is used to caress or massage the soft tissue. By "gum" it is meant the firm connective tissue covered by mucous membrane that envelops the alveolar arches of the jaw and surrounds the bases of the teeth. The amount of liquid medication which can be transferred to the teeth and/or soft tissue of a person's mouth can vary.

The solution, whether an antimicrobial solution, an antiseptic solution, an antibacterial solution, a combination of an antiseptic and an antibacterial or a liquid medication, can be absorbed onto the textured outer surface 24 of the floss device 10. By "liquid" it is meant a state of matter characterized by a readiness to flow, little or no tendency to disperse, and relatively high incompressibility.

It should be understood that the floss device 10 is usually formed or molded from clear, opaque or white resin. By "opaque" it is meant impenetrable by light; neither transparent nor translucent. Alternatively, the floss device 10 could be formed or molded from a colored resin.

It should also be understood that once a solution or liquid medication is absorbed onto a clear, opaque or white colored textured outer surface 24 of the floss device 10, that the solution or liquid medication may cause the floss device 10 to change color. The color of the floss device 10 can be changed to any known color. The floss device 10 could be changed to a pink, a red, a blue, a yellow, a purple, etc. The color change can be advantageous for it will provide a visual signal to the ultimate user that the floss device 10 contains a solution or a liquid medication. However, once the floss device 10 is colored by a solution or liquid medication, it is unlikely that all of the color will leave the floss device 10 even when a majority of the solution or liquid medication has been released from the floss device 10.

Another feature of the floss device 10 is that it can contain an essential oil that can contribute or convey a flavor. The essential oil can be absorbed by the textured outer surface 24 of the floss device 10 in a similar fashion as the solution or liquid medication is absorbed. Alternatively, the essential oil can be coated, sprayed, brushed or somehow be attached to the textured outer surface 24 of the floss device 10 in any manner known to those skilled in the art. The essential oil can convey a flavor which adds a distinctive taste or quality to the floss device 10. The flavor could be any known flavor. Examples of some flavors include but are not limited to lemon, lime, citrus, orange, bubblegum, mint, spearmint, etc. The presence of an essential oil which conveys a flavor in or on the floss device 10 can cause a person using the floss device 10 to keep the floss device 10 in his or her mouth for a longer period of time. This is beneficial in that it provides extra time for the solution or liquid medication to be transferred to the teeth and/or soft tissue of the person's mouth.

Another option is to impregnate or coat the floss device 10 with a specific essential oil that can convey a desirable smell or scent. A savory smell may be appetizing to the nose of a person. Again, this can be beneficial in that it causes a person to use the floss device 10 more often or to keep the floss device 10 in his or her mouth for a longer period of time.

During formation of the floss device 10, the material used to form the floss device 10 can be contacted with or immersed in a desired solution such that at least about 3, 4, 5, 6, 7, 8, 9, 10 or more percent by weight of the floss device 10 will be the weight of the solution or liquid medication absorbed onto the textured outer surface 24 of the floss device 10. Desirably, the floss device 10 can be contacted or immersed in a desired solution or liquid medication such that at least about 10% by weight of the floss device 10 will be the weight of the solution or liquid medication that is absorbed into the floss device 10. More desirably, the floss device 10 can be contacted or immersed in a desired solution or liquid medication such that at least about 12% by weight of the floss device 10 will be the weight of the solution or liquid medication that is absorbed onto the textured outer surface 24 of the floss device 10. Even more desirably, the floss device 10 can be contacted or immersed in a desired solution such that more than about 15% by weight of the floss device 10 will be the weight of the solution or liquid medication that is absorbed onto the textured outer surface 24 of the floss device 10.

It should be understood that about 18% will represent the upper amount of a solution or liquid medication that can be practically absorbed onto the textured outer surface 24 of the floss device 10.

The floss device 10 having an absorbed solution or liquid medication is designed to be used by inserting, probing and maneuvering the floss device 10 around a single tooth or between two adjacent teeth. The floss device 10 can do this because it is both flexible and durable.

The rounded tip 16 of the floss device 10 can be inserted, probed and maneuvered around the various teeth. A reciprocating action can also be obtained by moving the floss device 10 back and forth so that the pair of sides 22, 22 can breakup any plaque and/or tartar which has formed on the various teeth. By maneuvering the floss device 10 in between and around the outer periphery of each tooth, one can better remove such plaque and/or tartar then is currently possible by flossing with string. Furthermore, by using the first portion 12 of the floss device 10 to massage and caress the soft tissue of a user's mouth, the antimicrobial, the antiseptic, antibacterial, combination antiseptic/antibacterial solution or liquid medication can be delivered to the teeth and surrounding soft tissue of the person's mouth. The solution or liquid medication can leach out or be released from the floss device 10 on contact with the teeth and soft tissue. The movement of the floss device 10 within a person's mouth, as well as the bending, flexing and mechanical contact of the floss device 10 with the teeth and/or the surrounding soft tissue will cause the solution or liquid medication to be transferred from the floss device 10 to the teeth and surrounding soft tissue.

It should be understood that inserting the entire floss device 10 into a solution or liquid medication immediately upon its removal from a mold for a substantial period of time, such as for about 3 weeks, can cause the textured outer surface 24 of the floss device 10 to absorb from between about 10% to about 18% of the solution or liquid medication. The exact time that the floss device 10 needs to be immersed in a solution or liquid medication will depend upon the concentration and type of solution or liquid medication, the resin the floss device 10 is molded from, the size, shape and configuration of the floss device 10, the temperature of the solution or liquid medication, etc.

Lastly, the moisture and/or saliva present in a person's mouth may also contribute to the rate of transfer of the solution or liquid medication from the floss device 10 to the teeth and surrounding soft tissue. No test has been conducted to verify this phenomenon. The actual movement of the floss device 10 within a person's mouth will permit the solution or liquid medication to be quickly and efficiently transferred to the teeth, gums and surrounding soft tissue.

Method of Forming the Floss Device

A method of forming a floss device 10 will now be explained with reference to the flow diagram shown in FIG. 9. The floss device 10 is as described above. The floss device 10 has an arcuately shaped first portion 12 terminating in a rounded tip 16, and a second portion 14 secured to the first portion 12 at a securement surface or line 18 located opposite to the rounded tip 16. The floss device 10 is capable of being used to probe and maneuver about a single tooth or between two adjacent teeth of a person's mouth, as well as caressing and massaging the surrounding soft tissue. The method of forming the floss device 10 includes introducing a moldable material into a mold cavity. The moldable material can be any of the materials explained above. The moldable material can initially be in the form of solid pellets which can be placed in a hopper. The hopper can deliver the solid pellets to a heated portion of a molding machine where the solid pellets are transformed into a molten state. By "molten" it is meant to be made liquid by heat; to melt. Many thermoplastics, including Nylon 6 and Nylon 6, 6, have a melting point ranging somewhere between about 374° F. to about 663° F. (190° C. to about 350° C.).

The molding machine can vary in kind, type and configuration. Desirably, the molding machine is an injection molding machine. Alternatively, the molding machine could be a reaction injection molding machine. Those skilled in the molding art will be aware of various molding machines that could be used to mold the floss device 10.

In an injection molding machine, the moldable material will be introduced in a molten form into a mold cavity of the molding machine. The mold cavity can be formed from two or more members which cooperate together to enclose a hollow mold cavity. Usually, a mold cavity is constructed of two cooperating members, each forming a half of the finished product. Each of the two mold halves contains a sunken, hollow depression. The bottom or lower surface of each mold half resembles half of the outer surface of the finished product. The mold cavity can vary in size, shape and configuration.

The moldable material can be directed to flow into a closed mold cavity through an inlet opening and will completely fill the mold cavity. The mold in an injection molding machine usually is heated to a temperature above room temperature. Desirably, the mold is heated to a temperature of from between about 90° F. to about 170° F. More desirably, the mold is heated to a temperature of from between about 110° F. to about 150° F. Once the moldable material is present in the mold cavity, it will begin to cool and solidify. The time required for solidification will depend upon the composition of the moldable material, the temperature of the entering molten material, the temperature of the mold, the quantity of moldable material injected into the mold cavity, the size and shape of the mold cavity, whether the mold is cooled or chilled after the molten material is introduced into the mold cavity, etc. Typically a 400° F. molten material will start to cool and solidify once it is introduced into a mold cavity retained at a temperature from between about 90° F. to about 170° F. When the floss device 10 is formed from Nylon 6 and sized as described above, it is estimated that the time required for the molten material to solidify in the mold cavity will range from between about 5 seconds to about 60 seconds. Desirably, the time for the moldable material to solidify in the mold cavity into the floss device 10 will be less than about 60 seconds. More desirably, the time for the moldable material to solidify in the mold cavity into the floss device 10 will be less than about 45 seconds. Even more desirably, the time for the moldable material to solidify in the mold cavity into the floss device 10 will be less than about 30 seconds. Most desirably, the time for the moldable material to solidify in the mold cavity into the floss device 10 will be about 10 seconds.

It may also be advantageous to dry the plastic resin in a controlled environment for a period of time before it enters the mold. The reason for this is to make sure that the resin does not have a high concentration of moisture. Zero moisture is desirable for it will allow the molded floss device 10 to absorb the greatest amount of solution or liquid medication immediately upon its release from the mold cavity. The plastic resin can be dried at various temperatures but a temperature of from between about 210° F. to about 225° F. works well for Nylon 6. The plastic resin can be dried for various time periods. A time period of from between about 2 to about 4 hours is beneficial for Nylon 6.

It should be understood that the drying time and temperature can vary for different plastic resins. With a dry resin, one can immediately immerse the molded floss device 10 upon its release from the mold cavity in a solution or liquid medication.

Once the moldable material has solidified into the floss device 10, the mold cavity is opened and the floss device 10 is removed. The mold cavity can be constructed such that it will automatically open and close at set intervals. The molded floss device 10 can be ejected from the mold cavity by a push rod or by some other mechanical mechanism. Alternatively, the molded floss device 10 can be removed from the mold cavity by hand, by using an external tool, by the use of gravity or by a combination of two or more of these.

Immediately upon removal or ejection of the floss device 10 from the mold cavity, the floss device 10 can be immersed in a solution or liquid medication for a sufficient period of time. The solution or liquid medication can be any of the solutions or medications described above. Desirably, the solution is an antimicrobial solution. More desirably, the solution contains an antiseptic component, an antibacterial component, or a combination of an antiseptic component and an antibacterial component. The liquid medication can be any that is compatible with the plastic resin. One could use a polar solution, if desired. The solution or liquid medication can be maintained at room temperature, be below room temperature or be above room temperature when the floss device 10 is immersed therein. Desirably, the solution or liquid medication is maintained at or above room temperature.

Desirably, the floss device 10 is completely immersed in the solution or liquid medication. Alternatively, one could immerse only a portion of the floss device 10 in the solution or liquid medication. Another option is to immerse only a portion of the first portion 12 in the solution or liquid medication. This portion would include the rounded tip 16 and the pair of sides 22, 22. Another way of stating this is with reference to FIG. 4, wherein a portion of the first portion 12 from the rounded tip 16 to the point where the cross-sectional line 8-8 is located could be immersed in the solution or liquid medication. Since the floss device 10 is relatively small, it has been found that a total submersion of the floss device 10 in the solution or liquid medication is the most efficient and economical.

The time that the floss device 10 is immersed in the solution or liquid medication can vary. The time can vary from a few seconds, a few hours, a couple of days or even several weeks depending upon the type of solution or liquid medication and the amount one wishes the floss device 10 to absorb. The time period will depend on how much of the solution or liquid medication one wants the floss device 10 to absorb by weight. The concentration of the solution or liquid medication can also impact the amount of time the floss device 10 needs to be immersed. It has been found that over a period of about 3 weeks, the floss device 10 can absorb from between about 10% to about 18% by weight of the solution or medication when the floss device 10 is molded from Nylon 6 and the solution is similar to LISTERINE®. This means that the initial weight of the floss device 10 will increase by from between about 10% to about 18%. It has been found that the floss device 10 is effective in transferring solution or liquid medication to the teeth and adjoining soft tissues of a person's mouth when the floss device 10 initially contains at least about 10% by weight of the solution or liquid medication. Desirably, the floss device 10 will contains at least about 11% by weight of the solution or liquid medication. More desirably, the floss device 10 will contains at least about 12% by weight of the solution or liquid medication. Even more desirably, the floss device 10 will contains at least about 13% by weight of the solution or liquid medication. A floss device 10 that has absorbed at least about 10% by weight of the solution or liquid medication can be used once and then be discarded. However, the floss device 10 could be used multiple times and still be useful in transferring the solution or liquid medication onto a person's teeth and the surrounding soft tissue. A purchaser of the floss device 10 could initially use and then reuse the floss device 10 for up to two to three days before there is no more solution or liquid medication to be transferred to his or her teeth and surrounding soft tissue. It should be noted that this time period is contingent upon the time the floss device 10 is present in a person's mouth, the temperature at which the floss device 10 is stored, the humidity at which the floss device 10 is stored, the located where the floss device 10 is stored, etc.

It should be noted that the floss device could be sold without having absorbed any solution or liquid medication. The floss device 10 can be used dry to probe and maneuver about a single tooth or between two adjacent teeth of a person's mouth, as well as caressing and massaging the surrounding soft tissue. In this scenario, the floss device 10 will be used to remove foreign objects lodged between adjacent teeth and to breakup plaque and/or tartar that has built up on the teeth. In addition, the dry floss device 10 can be fully or partially be immersed or dipped into a container or vial of a solution or liquid medication immediately before it is to be used by a consumer. In this scenario, the consumer would immerse or dip the floss device 10 into a solution or liquid medication and then immediately transfer the solution or liquid medication onto his or her teeth and the surrounding soft tissue. In this scenario, the solution or liquid medication is not absorbed into the textured outer surface 24 of the floss device 10 but instead is temporarily retained on the textured outer surface 24 before it is transferred. For a floss device 10 that will be used only once, it is anticipated that the floss device 10 would adequately work for some solutions and liquid medications when the textured outer surface 24 temporarily retains as little as about 2, 3, 4, 5, 6, 7, 8 or 9 percent by weight of a solution or liquid medication.

For a floss device 10 that can be used more than once and can efficiently transfer an antimicrobial solution, such as LISTERINE® to a person's teeth and surrounding soft tissue, the floss device 10 should have absorbed at least about 10% by weight of the solution or liquid medication. Desirably, the floss device 10 will have absorbed at least 11% by weight of the solution or liquid medication. More desirably, the floss device 10 should have absorbed at least about 12% by weight of the solution or liquid medication. Even more desirably, the floss device 10 should have absorbed from between about 10% to about 18% by weight of the solution or liquid medication. Most desirably, the floss device 10 should have absorbed from between about 10% to about 15% by weight of the solution or liquid medication.

An alternative to immersing the just molded floss device 16 in a solution or liquid medication is to store the dry floss device 10 in a moisture free environment after it is formed. By storing the floss device 10 in a dry, moisture free environment, one can later subject the floss device 10 to a solution or liquid medication. The solution or liquid medication can be absorbed into the floss device 10 by immersion for the required time period. Alternatively, the floss device 10 may be placed in an enclosed container and a gaseous solution can be introduced into the container at a predetermined pressurize value. Those skilled in the art will be aware of other ways in which a solution or liquid medication can be absorbed into the floss device 10 either immediately after exiting a mould or at a certain time thereafter.

It should be understood that it is desirable to mold the floss device, have it absorb a given amount of a solution or liquid medication, and then package the floss device 10 for sale to the ultimate consumer.

After the floss device 10 has absorbed a sufficient amount or quantity of a solution or liquid medication, the floss device 10 can be packaged. Desirably, the package is a moisture barrier package which can contain one or more layers of a moisture barrier material. Aluminum foil forms a good moisture barrier. Furthermore, the floss device 10 can be packaged in a moisture barrier package along with additional solution or liquid medication. The additional solution or liquid medication in the package can be identical, similar to or be different from the solution or liquid medication which was initially absorbed by the floss device 10. Desirably, the additional solution or liquid medication in the package is of the same composition as the solution or liquid medication that was initially absorbed by the floss device 10. However, the concentration of the added solution or liquid medication need not be the same as what was initially absorbed by the floss device 10.

As mentioned above, the solution or liquid medication can vary in composition and concentration. The solution can be an antimicrobial solution, an antiseptic solution, an antibacterial solution, a combination of an antiseptic compound and an antibacterial compound, etc. The medication can also vary in composition and concentration.

Lastly, it should be understood that the floss device 10 can be immersed or dipped into a solution which includes both antiseptic and antibacterial components. The floss device 10 can be immersed or dipped for a period of time sufficient for the floss device 10 to absorb from between about 10% to about 18% by weight of the solution or liquid medication. Desirably, the floss device 10 can absorb from between about 10% to about 17% by weight of the solution or liquid medication. More desirably, the floss device 10 can absorb from between about 10% to about 16% by weight of the solution or liquid medication. Even more desirably, the floss device 10 can absorb from between about 10% to about 15% by weight of the solution or liquid medication.

Method of Using the Floss Device

A method of using the floss device 10 will now be explained with reference to the flow diagram shown in FIG. 10. The floss device 10 is as described above. The floss device 10 has an arcuately shaped first portion 12 terminating in a rounded tip 16, and a second portion 14 secured to the first portion 12 at a securement surface or line 18 located opposite to the rounded tip 16. The floss device 10 is capable of being used to probe or maneuver around a single tooth or between two adjacent teeth, as well as caress and massage the surrounding soft tissue of a person's mouth. The floss device 10 can be used dry or wet after having absorbed a solution or liquid medication. When the floss device 10 is wet, it is capable of transferring, releasing and delivering the solution or liquid medication to the teeth and surrounding soft tissue of the person's mouth. The solution can be an antimicrobial, an antiseptic, an antibacterial, a combination of an antiseptic compound and an antibacterial compound, etc.

The method of using the floss device 10 includes the steps of inserting, probing, maneuvering or manipulating the rounded tip 16 of the floss device 10 around a single tooth or between a first of two adjacent teeth. By "inserting, probing, maneuvering or manipulating" it is meant to operate or control the movement of the floss device 10 by skilled hands. The floss device 10 can also be used to massage and caress the surrounding soft tissue. The floss device 10 is constructed and designed to dislodge any foreign objects, such as small pieces of food, lodged between the teeth. The floss device 10 will also assist in mechanically breaking up plaque and/or tartar that may have accumulated on the outer surfaces of the teeth. The pair of sides 22, 22 is tapered relative to the rounded tip 16 and each has a textured outer surface 24 which is particularly adapted to breaking up plaque and removing tartar from the outer periphery of the teeth.

When the floss device 10 has absorbed a solution or liquid medication, such solution or liquid medication can be transferred, released and deposited onto the teeth and the surrounding soft tissue. The floss device 10 can be manipulated, moved and maneuvered between the first of two adjacent teeth for any period of time. The time can vary from a few seconds to a minute or more. The floss device 10 can also be used to caress, massage and gently rub the gums and soft tissues surrounding the teeth for any desired time period.

The orientation of the floss device 10 can vary during use. Generally, when probing between the upper teeth of a person with the floss device 10, the arcuate first portion 12 can be manipulated to point downwardly, as is depicted in FIG. 1. When probing between the lower teeth of a person with the floss device 10, the arcuate first portion 12 can be manipulated to point upward. However, since the spacing between certain teeth on different individuals can vary, one can manipulate, turn or orient the floss device 10 in a variety of positions so that it best accommodates the situation at hand. In addition, the convex top surface, the concave bottom surface and the pair of sides 22, 22 of the first portion 12 of the floss device 10 can be used to further caress and massage the gums and soft tissue located above, below or between the teeth. The floss device 10 is capable of dislodging any food particles stuck between adjacent teeth. In addition, the floss device 10 can be used to mechanically floss between adjacent teeth much like string floss is presently used today.

The floss device 10 can be moved in and out, up and down, or be reciprocated back and forth between two adjacent teeth so that the pair of sides 22, 22, located rearward of the rounded tip 16, can rub or scrub the outer perimeters of the teeth and break up any plaque and/or tartar that may have accumulated thereon. The rubbing or scrubbing of the teeth with the textured outer surface 24 produces a mechanical action that can break up the plaque and/or tartar. Furthermore, the solution or liquid medication that was initially absorbed onto the floss device 10 can be transferred and released such that it will be removed from the floss device 10. The absorbed solution or liquid medication can be released in any known manner. The solution or liquid medication is then free to chemically act upon any plaque and/or tartar that may be present on the teeth and treat the surrounding soft tissue. The solution can kill microorganisms or inhibits their growth. Depending upon the composition of the solution, the solution may be able to prevent infection by inhibiting the growth of microorganisms or inhibits bacterial growth or even kill the bacteria. The solution is released from the floss device 10 over time such that it can leach or percolate out or exit the floss device 10 in a controlled fashion. By "leach" it is meant to remove soluble or other constituents by the action of a percolating liquid. Depending upon the amount of solution or liquid medication that was initially absorbed onto the floss device 10, the solution or liquid medication may be released from the floss device 10 over a period of days, such that the floss device 10 can be used several times before it is discarded. If the floss device 10 has absorbed a liquid medication, the liquid medication can be released to treat the teeth and/or surrounding soft tissue of the person's mouth. The frequency of applying the liquid medication to the soft tissue will depend upon the kind and type of liquid medication being released by the floss device 10.

It should be understood that a semi solid medication, such as a paste, can also be administered to the teeth and the surrounding soft tissue of a person's mouth by the floss device 10.

Once a person has used the floss device 10 to probe around or between a first of two adjacent teeth, he or she can then reposition, maneuver and manipulate the floss device 10 between a second of two adjacent teeth, as well as caress and massage the surrounding soft tissue. Again, the floss device 10 can be used to remove any foreign objects lodge therebetween the second of the two adjacent teeth, such as food particles. The floss device 10 can also break up any plaque and/or tartar that may have accumulated on the outer surfaces of these teeth. The floss device 10 can also be used to caress and massage the surrounding soft tissue in the person's mouth. The user can continue to reposition, maneuver and manipulate the floss device 10 until all of his or her teeth have been flossed and cleaned. Desirably, all the teeth will be contacted with the floss device 10, including the outer surfaces of the last two molars, located in both the upper and lower jaw. A person may elect to use the floss device 10 to floss between some or all of his or her teeth. A person can and should floss around each and every tooth.

It should be understood that the floss device 10 can also be used to probe around and between dentures, partials and teeth containing crowns or caps.

A major difference between the floss device 10 of this invention and the standard string floss is that the floss device 10 provides both a mechanical action and a chemical action in breaking up and removing plaque and/or tartar because it has the ability to release a solution or liquid medication which can chemically act upon such plaque and/or tartar. Standard string floss does not have the ability to release an antimicrobial solution or any other kind of solution which can kill or inhibit the growth of microorganisms. Likewise, string floss does not contain a medication that can be transferred to the teeth or the surrounding soft tissue.

After a person has used the floss device 10, there is no need to rinse his or her mouth with water and/or with an antimicrobial solution, such as LISTERINE®. Such rinsing would dilute the solution or medication that has been transferred to the teeth and the surrounding soft tissue. By allowing the solution or medication to remain on the teeth and on the surrounding soft tissue, the solution or medication can continue to work to combat infections, and prevent or limit the buildup of plaque and/or tartar.

Lastly, a person should responsibly discard the used floss device 10 in an acceptable waste container. The floss device 10 can be used once or it can be used several times before it has to be discarded. Some people may prefer to use it only once. The floss device 10 can be placed in a standard waste or trash container present in most bathrooms. The floss device 10 can also be used outside of the bathroom. If used at various locations other than in a bathroom, the user should properly dispose of the floss device 10 in a nearby trash receptacle. The floss device 10 is not meant to be recycled since it may have food particles stuck to it. A used floss device 10 will also be contaminated with bacteria from a user's mouth. Furthermore, a floss device 10 that had absorbed a solution or liquid medication may still retain a small amount of such solution or liquid medication and for this reason, should not be recycled.

Protocol for Testing of Antiseptic Floss Device also Identified as RXPIX

The procedure for testing and findings are shown in the following pages.

Protocol for Testing of Antimicrobial RXPIX

1. Overview

For each sample three replicate experiments were preformed. Briefly, a drop of the bacterium *E. Coli* (strain DH5α) was mixed with a small amount of a medium (Luria-Bertani Broth, or LB Broth) and allowed to exchange fluid with the floss device 10, which is named "RXPIX" for identification purposes in the following tests, for 15 minutes. After this period of time, 2 ml of LB Broth was added to each test tube and the bacteria were allowed to grow for 20 hours at 37° C. Observing the turbidity of the broth at this time assessed bacterial viability. Bacterial viability was also assessed analytically by measuring the absorbance of visible light (600 nm).

2. Procedure

A. On day 1, a frozen stock of DH5α was thawed and used to inoculate 5 ml of LB Broth. The LB Broth was incubated at 37° C. for 24 hours and bacterial growth was observed as an increase in turbidity. A small amount (~50 micro liters) of bacterial medium was removed for use in this experiment.

B. On Day 2, 1 micro liter of *E. Coli* cells was transferred to each 12×75 mm round bottom test tube for antimicrobial testing. In addition, 5 micro liters of fresh LB Broth were added to each test tube to allow for fluid exchange. Finally, the RXPIX were removed from their respective fluid-filled containers, dried to remove excess fluid, and inserted into the round-bottom test tubes, tip first, to allow for fluid exchange between the medium, the bacteria, and the tip of the RXPIX. The test tubes were then agitated at room temperature for 15 minutes to ensure adequate fluid exchange and to allow the antimicrobial to take effect.

C. After 15 minutes of agitation, 2 ml of LB Broth was added to each round-bottom test tube. The test tubes were then transferred to a 37° C. incubator and shaken at 275 cycles/minute for a period of 20 hours.

D. After 20 hours of incubation, bacterial viability was assessed.

Visually turbidity of the LB Broth indicated bacterial growth (and therefore negligible antimicrobial activity). Clarity of the LB Broth indicated the absence of bacterial growth and therefore robust antibacterial activity.

E. To further characterize bacterial growth, the absorbance of 600 nm visible light was used to analytically measure turbidity. The broth from each sample was measured with a spectrophotometer equipped with a lamp emitting visible light.

3. Results

Bacterial growth occurred in test tubes that were exposed to unsoaked RXPIX. Bacterial growth also occurred in test tubes that were exposed to only water (positive control). No bacterial growth occurred in test tubes that were incubated with treated RXPIX. Furthermore, no bacterial growth occurred in test tubes that were incubated with 70% ethanol (negative control). Detailed results (both digital pictures and spectrophotometric readings) are attached.

4. Conclusions

The RXPIX are bactericidal and exhibit potent and specific antimicrobial activity.

Brief Description of Test Sets Disclosed and Shown

FIG. 11—Triple testing inoculated broth vials (test tubes) 1, 2, 3, 4, 5 and 6. This is a negative control showing vials of broth and each vial inoculated with bacteria. The turbidity indicates "bacterial growth" in a vial. In this image, all the vials (1, 2, 3, 4, 5 and 6) show turbidity.

Figure 12:
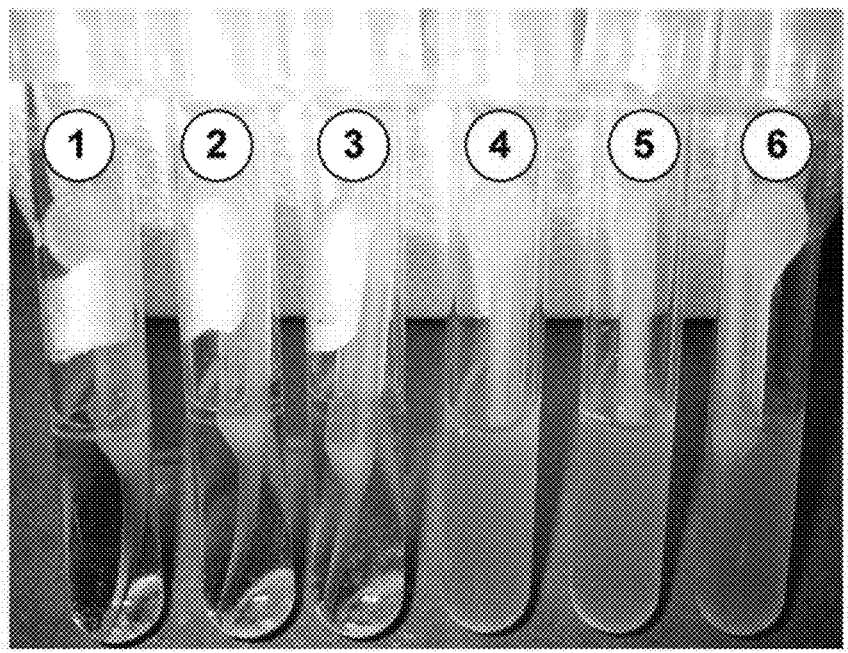
FIG. 12 is a photograph of six test tubes.

FIG. 12—Triple test showing sterility "no turbidity" of inoculated broth vials plus an antiseptic floss device in the vials 1, 2 and 3. The turbidity of the inoculated broth in the vials 4, 5 and 6 is still present since the floss devices in these vials did not contain an antiseptic. Antiseptic of mint mouthwash contained on floss devices in the vials 1, 2 and 3.

Figure 13:
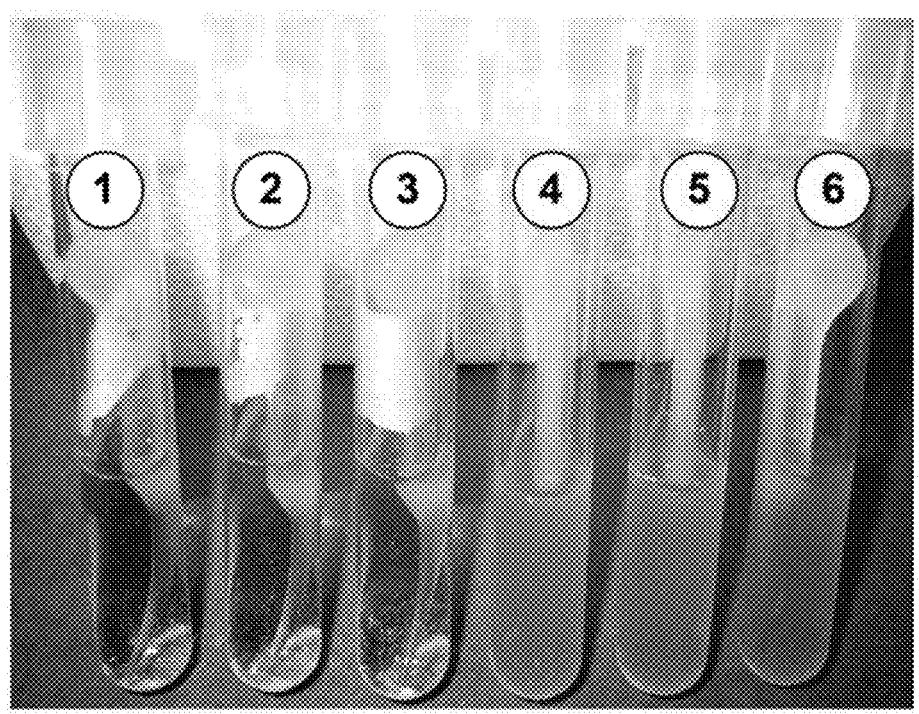
FIG. 13 is a photograph of six test tubes.

FIG. 13—This is a duplicate test of FIG. 12.

Figure 14:
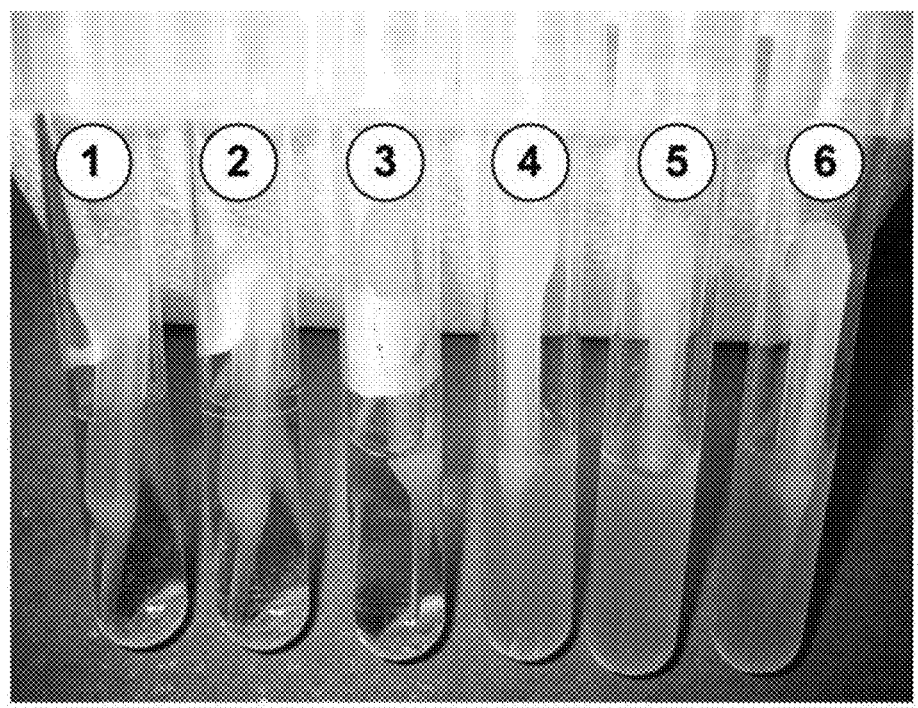
FIG. 14 is a photograph of six test tubes.

FIG. 14—This is a duplicate test of FIG. 12, but with CITRUS mouthwash.

Figure 15:
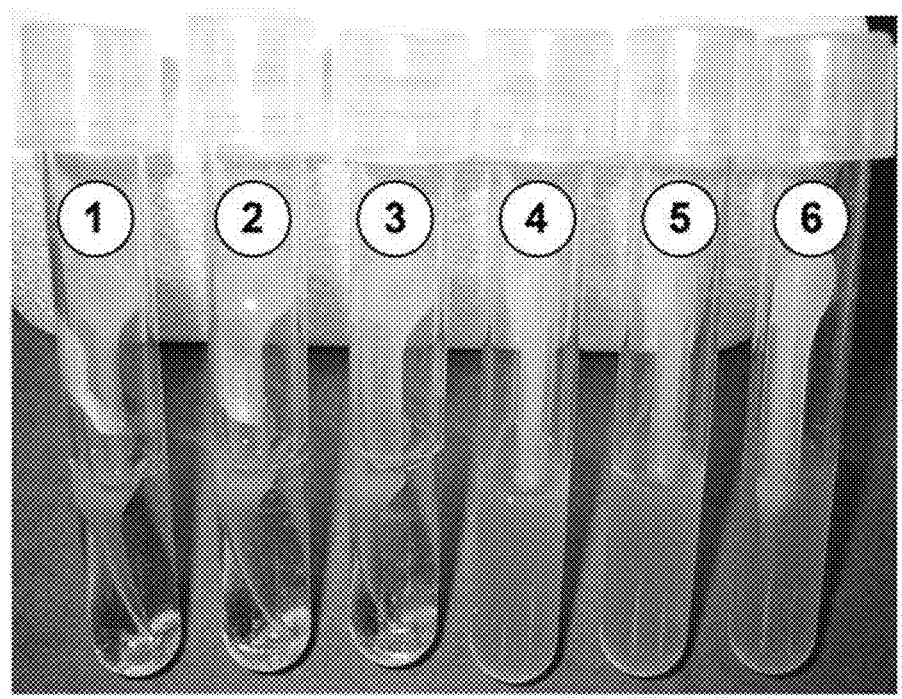
FIG. 15 is a photograph of six test tubes.

FIG. 15—This is a duplicate test of FIG. 14, with MINT mouthwash.

Figure 16:
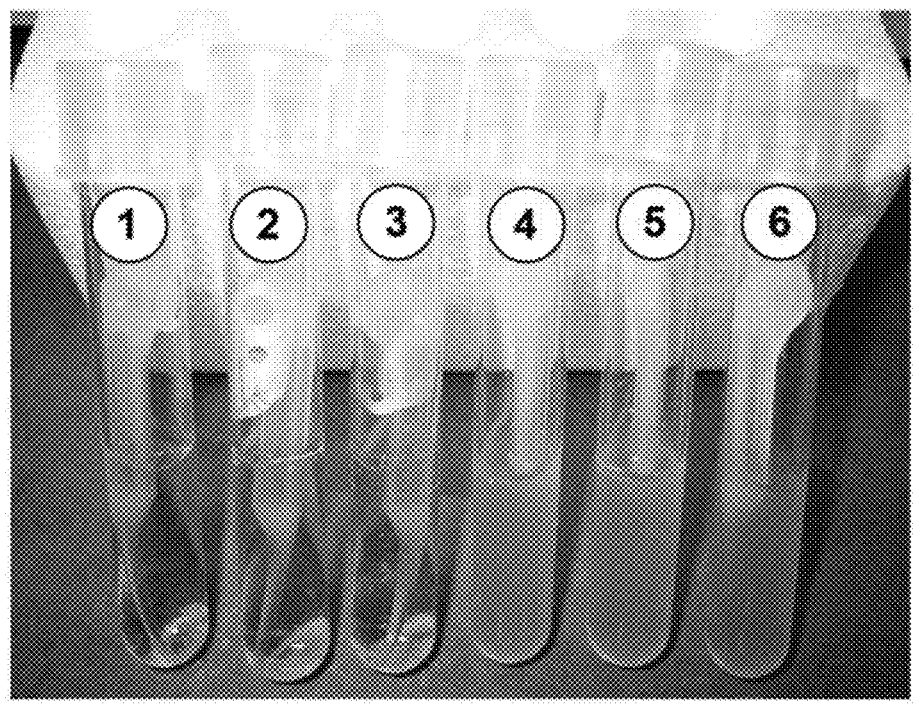
FIG. 16 is a photograph of six test tubes.

FIG. 16—This is a duplicate procedure of FIG. 15 with CITRUS mouthwash plus 0.5% sanguinaria contained on the floss device placed in vials 1, 2 and 3.

Figure 17:
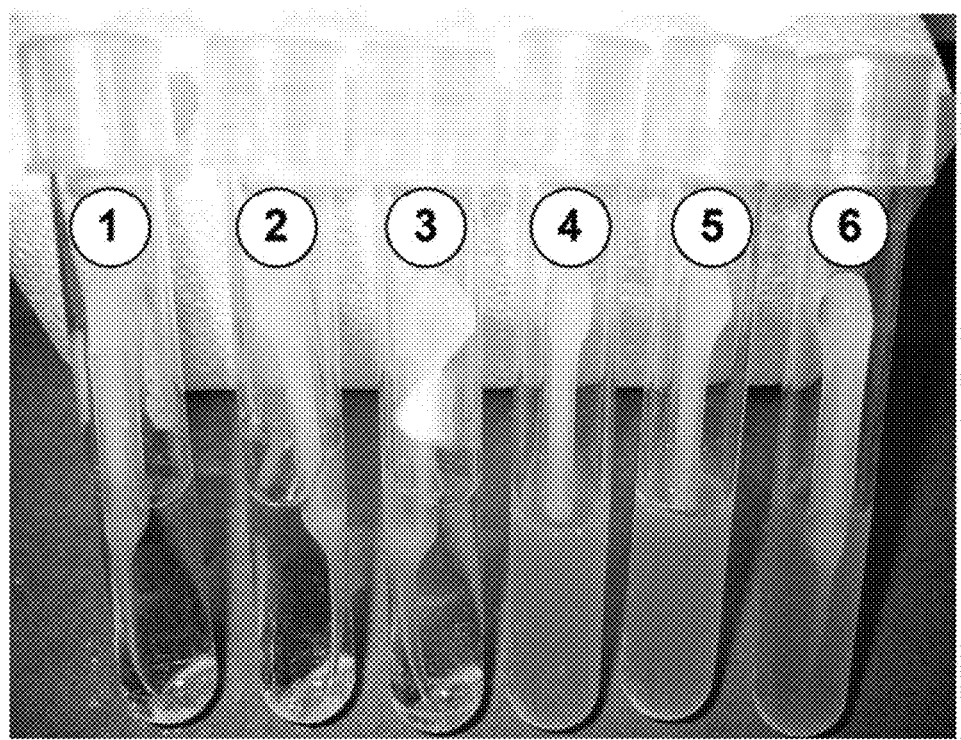
FIG. 17 is a photograph of six test tubes.

FIG. 17—Floss devices immersed in 90% ethyl alcohol, air dried and floss devices added to vials 1, 2 and 3.

Figure 18:
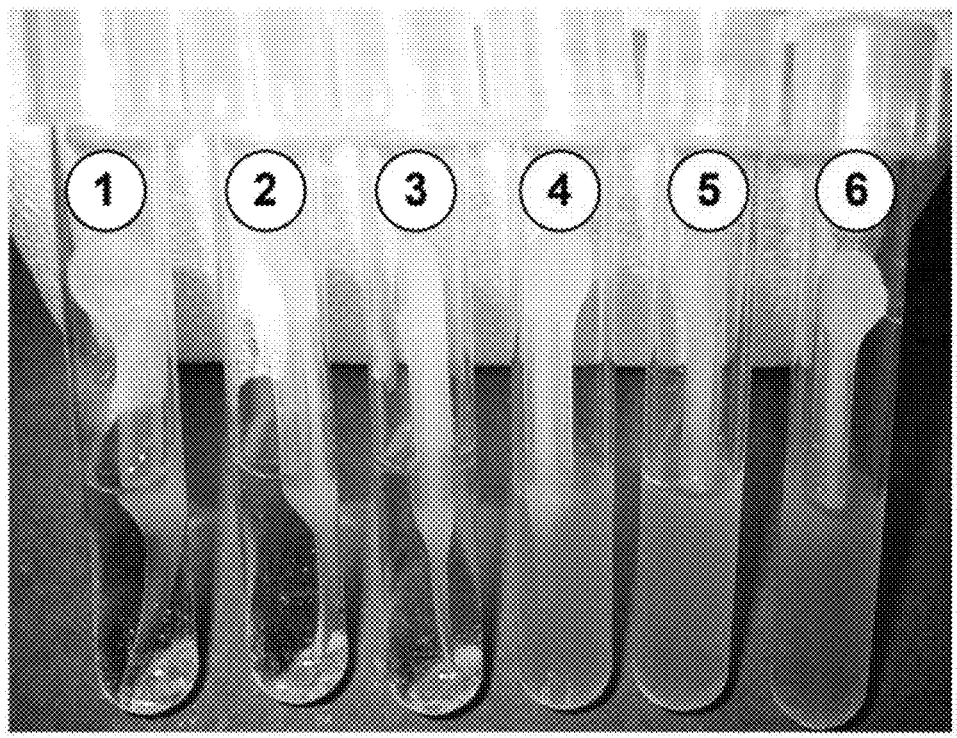
FIG. 18 is a photograph of six test tubes.

FIG. 18—This is a duplicate procedure of FIG. 17.

Figure 19:
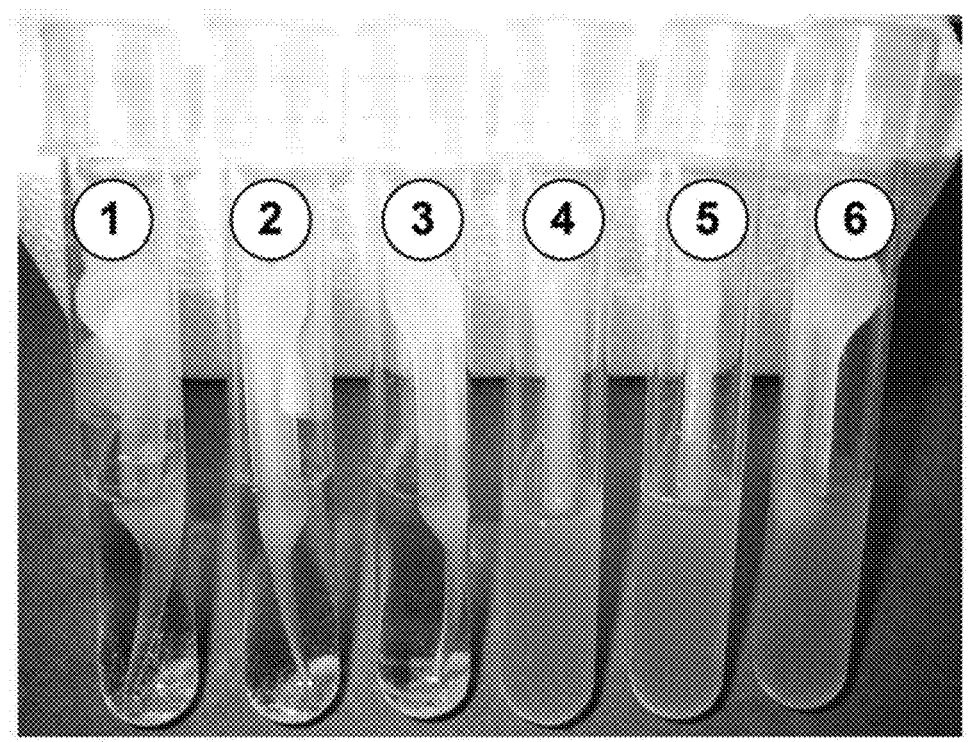
FIG. 19 is a photograph of six test tubes.

FIG. 19—Floss devices immersed in 90% ethyl alcohol, air dried plus 0.5% sanguinaria, added to vials 1, 2, and 3.

Figure 20:
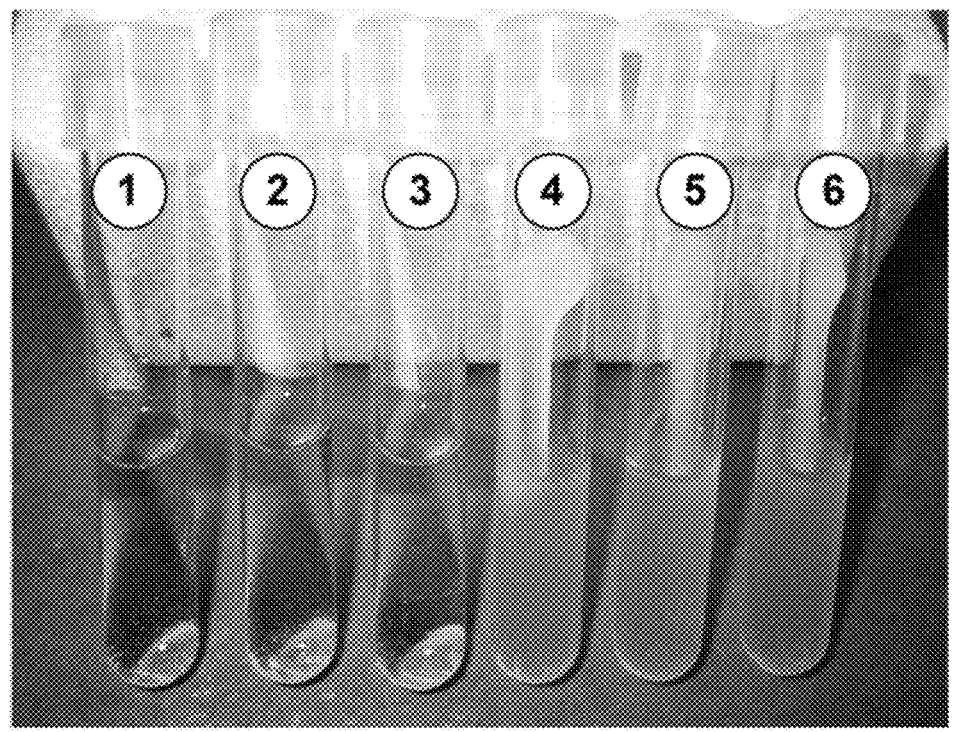
FIG. 20 is a photograph of six test tubes.

FIGS. 20—200 micro liters of 70% ethyl alcohol added to each inoculated vial 1, 2, and 3, as a negative control (not showing bacterial growth), but bacterial growth shown by turbidity of vials 4, 5 and 6.

Figure 21:
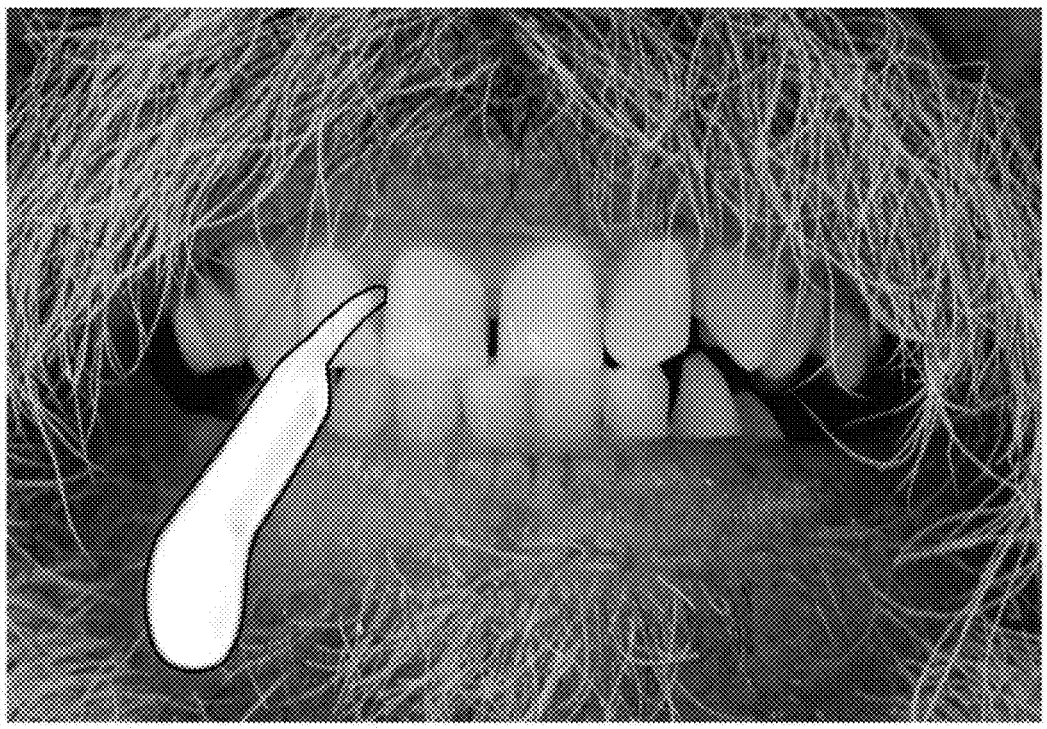
FIG. 21 is a photograph of the floss device being inserted between two adjacent teeth in a person's mouth.

FIG. 21—A floss device containing antiseptic/antibacterial shown in use in vivo (human mouth).

Description of Antiseptic Solutions Used in Above Described Protocol

Mint mouthwash—EQUATE® antiseptic blue mint mouth rinse containing as active ingredients: Eucalyptol 0.092%: Menthol 0.042%; Methyl salicylate 4.060%; and Thymol 0.064% Inactive ingredients are: water, alcohol 21.6%; sorbitol solution, flavor, poloxamer 407; benzoic acid; sodium saccharin, sodium benzoate; and FD&C green no. 3. The Citrus orange color mouth wash—EQUATE® antiseptic citrus mouth rinse has the same active ingredients as the above described Mint mouthwash. The inactive ingredients of this Citrus mouthwash are: water, alcohol 21.6%; sorbitol solution, flavor, poloxamer 407; benzoic acid; sucralose and/or sodium saccharin, sodium benzoate; and cochineal extract.

The floss device 10 is called RXPIX for identification purposes in the protocol and is synonymous with products molded or formed of Nylon 6, readily absorbs moisture up to 8% of its weight and it is this moisture uptake by Nylon 6 that is the gist of this invention.

To mold Nylon 6 into a floss device requires heating of Nylon 6 to a plastic state then injecting it into a mold cavity. The floss device moldings of the Nylon 6 are immediately captured, on ejection from the molding cavities, and protected from absorption of moisture and water. After capture of the Nylon 6 floss device 10 from the molding cavities and protected from moisture absorption, the floss devices 10 are immersed in a liquid antiseptic/antibacterial solution. At this time, the antiseptic/antibacterial permeates the floss devices 10, after which the floss devices 10, immersed in the antiseptic are dried and ready for subsequent use as an antiseptic/antibacterial floss device in the human mouth invivo, between the teeth and/or on the gums.

In the protocol results described above, the turbidity shows bacterial growth, and clarity shows no bacterial growth. The clarity shows efficacy of the procedure and the protocol described, including molded Nylon 6 absorption of an antiseptic/antibacterial solution, and subsequently leachable from the Nylon 6 in a liquid media, or as used in vivo, in the human mouth as a floss device 10.

While the invention has been described in conjunction with a specific embodiment, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

I claim:

1. A floss device consisting of nylon 6 material having a length measured along a longitudinal central axis, a height measured along a vertical central axis and a thickness measured along a transverse central axis, said floss device having a first portion joined to a second portion along said length, said first portion having an arcuate configuration which curves along said vertical central axis and tapers inward along said transverse central axis to a narrow dimension and terminates in a rounded tip, said rounded tip having a height which includes a first radius, a spaced apart second radius and a rounded surface therebetween, said rounded surface being a portion of a circular arc, said second portion is linear and terminates in an enlarged distal end having a circular configuration which is designed to be grasped between a person's thumb and index finger, said enlarged distal end having a pair of oppositely aligned, circular indentations formed therein, said enlarged distal end being aligned parallel to said height of said rounded tip, and said enlarged distal end with said pair of circular indentations facilitating manipulation of said floss device by a person to probe around and between a person's teeth, said floss device has an textured outer surface which extends rearward from said rounded tip over at least a portion of said floss device and said textured outer surface has a micro-contoured profile which increases surface area and facilitates the temporary retention of a solution which can be transferred to the teeth and the surrounding soft tissue of a person's mouth.

2. The floss device of claim 1 wherein said first portion is flexible and resilient, and said textured outer surface circumferentially surrounds said floss device and extends rearward from said rounded tip for at least about 10% of the length of said floss device, and said floss device can retain a volume of said solution exceeding 10% by weight of said floss device.

3. The floss device of claim 1 further comprising having a maximum moisture saturation of about 2.7%, and said solution is an antimicrobial, an antiseptic or an antibacterial.

4. The floss device of claim 1 wherein said textured outer surface extends 360 degrees around at least a portion of said floss device and said enlarged distal end has a circular configuration which extends parallel to said vertical central axis and extends downward in the same direction as said rounded tip.

5. The floss device of claim 1 wherein said textured outer surface extends rearward from said rounded tip and surrounds said entire first portion, said rounded tip has a height, and said enlarged distal end is aligned parallel to said height of said rounded tip.

6. The floss device of claim 1 wherein at least a portion of said first portion includes a pair of sides which extend rearward from said rounded tip along said longitudinal central axis, said pair of sides tapering inward towards one another and terminating approximate said rounded tip, said pair of sides being aligned parallel to said vertical central axis, and each of said pair of sides having a textured outer surface used to mechanically breakup plaque and/or tartar present on a person's teeth.

7. A floss device consisting of a nylon 6, 6 material having a length measured along a longitudinal central axis, a height measured along a vertical central axis and a thickness measured along a transverse central axis, said floss device having a first portion joined to a second portion along said length, said first portion having an arcuate configuration which curves along said vertical central axis and tapers inward along said transverse central axis to a narrow dimension and terminates in a rounded tip, said rounded tip having a height which includes a first radius, a spaced apart second radius and a rounded surface therebetween, said rounded surface being a portion of a circular arc, said second portion is linear and terminates in an enlarged distal end having a circular configuration which is designed to be grasped between a person's thumb and index finger, said enlarged distal end having a pair of oppositely aligned, circular indentations formed therein, said enlarged distal end being aligned parallel to said height of said rounded tip, and said enlarged distal end with said pair of circular indentations facilitating manipulation of said floss device by a person to probe around and between a person's teeth, said floss device has an textured outer surface which extends rearward from said rounded tip over at least a portion of said floss device and said textured outer surface has a micro-contoured profile which increases surface area and facilitates the temporary retention of a solution which can be transferred to the teeth and the surrounding soft tissue of a person's mouth.

8. The floss device of claim 7 wherein said first radius is equal to said second radius, and said first and second radiuses are spaced apart from one another by said rounded surface.

9. The floss device of claim 7 wherein said floss device has an upside down, teardrop profile with the widest part being on the top, at the location where said first portion is joined to said second portion.

10. The floss device of claim 7 wherein said thickness is non-uniform along said length and said pair of sides extends rearward from said rounded tip over a distance of from between about 0.1 inches to about 0.75 inches.

11. The floss device of claim 7 wherein an essential oil is absorbed onto said textured outer surface to convey a flavor.

12. The floss device of claim 7 wherein each of said pair of circular indentations has a diameter ranging from between about 0.20 inches to about 0.75 inches, and each of said pair of circular indentations has a depth, measured along said transverse central axis, of at least about 0.01 inches.

13. The floss device of claim 12 wherein each of said pair of circular indentations has a depth ranging from between about 0.01 inches to about 0.05 inches.

14. A method of forming a floss device, said floss device consisting essentially of a nylon-6 material having a length measured along a longitudinal central axis, a height measured along a vertical central axis and a thickness measured along a transverse central axis, said floss device having a first portion joined to a second portion along said length, said first portion having an arcuate configuration which curves along said vertical central axis and tapers inward along said transverse central axis to a narrow dimension and terminates in a rounded tip, said rounded tip having a height which includes a first radius, a spaced apart second radius and a rounded surface therebetween, said second portion is linear and terminates in an enlarged distal end which is designed to be grasped between a person's thumb and index finger, said enlarged distal end having a pair of oppositely aligned indentations formed therein, said enlarged distal end being aligned parallel to said height of said rounded tip, and said enlarged distal end with said pair of indentations facilitating manipulation of said floss device by a person to probe around and between a person's teeth, and said floss device has a textured outer surface which extends rearward from said rounded tip over at least a portion thereof, said textured outer surface having a micro-contoured profile which increases surface area and facilitates the retention of a quantity of a solution or medication, said method comprising the steps of:
 a) introducing a moldable plastic resin into a mold cavity and molding a floss device;
 b) allowing said molded floss device to solidify;
 c) removing said solidified floss device from said mold cavity; and
 d) immersing said solidified floss device in a solution or a liquid medication for a sufficient amount of time so that said textured outer surface can absorb a predetermined amount of said solution or liquid medication.

15. The method of claim 14 further comprising drying said plastic resin before it is introduced into a mold cavity.

16. The method of claim 14 further comprising packaging said floss device after said textured outer surface has absorbed said solution or liquid medication in a moisture barrier package.

17. The method of claim 16 further comprising packaging said floss device after said textured outer surface has absorbed said solution or liquid medication in a moisture barrier package containing additional solution or liquid medication.

18. The method of claim 14 further comprising having said floss device absorb said solution or medication immediately upon removal of said floss device from a mold.

19. A method of using a floss device, said floss device consisting of a nylon 6 material and a solution or medication having a length measured along a longitudinal central axis, a height measured along a vertical central axis and a thickness measured along a transverse central axis, said floss device having a first portion joined to a second portion along said length, said first portion having an arcuate configuration which curves along said vertical central axis and tapers inward along said transverse central axis to a narrow dimension and terminates in a rounded tip, said rounded tip having a height which includes a first radius, a spaced apart second radius and a rounded surface therebetween, said rounded surface being a portion of a circular arc, a portion of said first portion having a pair of oppositely aligned sides extending along said longitudinal central axis, said pair of sides tapering inward towards one another and terminating approximate said rounded tip, said pair of sides being aligned parallel to said vertical central axis, and said second portion is linear and terminates in an enlarged distal end having a circular configuration which is designed to be grasped between a person's thumb and index finger, said enlarged distal end having a pair of oppositely aligned, circular indentations formed therein, said enlarged distal end being aligned parallel to said height of said rounded tip, and said enlarged distal end with said pair of indentations facilitating manipulation of said floss device by a person to probe around and between a person's teeth, and said floss device has a textured outer surface which extends rearward from said rounded tip over at least a portion thereof, said textured outer surface having a micro-contoured profile which increases surface area and facilitates the retention of a quantity of said solution or medication, said method comprising the steps of:
a) manipulating said rounded tip around and between a first of two adjacent teeth to remove any foreign objects lodged therebetween and allowing said pair of sides to breakup plaque and/or tartar present on said teeth, and transferring said solution or medication to said first of said two adjacent teeth and the surrounding soft tissue of a person's mouth;
b) repositioning said floss device and manipulating said rounded tip around and between a second of two adjacent teeth to remove any foreign objects lodged therebetween and allowing said pair of sides to breakup plaque and/or tartar present on said teeth, and transferring said solution or medication to said second of said two adjacent teeth and the surrounding soft tissue of a person's mouth; and
c) repositioning said floss device and manipulating said rounded tip around and between additional pairs of teeth to remove any foreign objects lodged therebetween and allowing said pair of sides to breakup plaque and/or tartar present on said teeth, and transferring said solution or medication to said additional pair of teeth and the surrounding soft tissue of a person's mouth.

20. The method of claim 19 further comprising discarding said floss device in an acceptable waste container.

21. A floss device consisting of nylon-9 having a length measured along a longitudinal central axis, a height measured along a vertical central axis and a thickness measured along a transverse central axis, said floss device having a first portion joined to a second portion along said length, said first portion having an arcuate configuration which curves along said vertical central axis and tapers inward along said transverse central axis to a narrow dimension and terminates in a rounded tip, said rounded tip having a height which includes a first radius, a spaced apart second radius and a rounded surface therebetween, said rounded surface being a portion of a circular arc, said second portion is linear and terminates in an enlarged distal end having a circular configuration which is designed to be grasped between a person's thumb and index finger, said enlarged distal end having a pair of oppositely aligned, circular indentations formed therein, said enlarged distal end being aligned parallel to said height of said rounded tip, and said enlarged distal end with said pair of circular indentations facilitating manipulation of said floss device by a person to probe around and between a person's teeth, said floss device has an textured outer surface which extends rearward from said rounded tip over at least a portion of said floss device and said textured outer surface has a micro-contoured profile which increases surface area and facilitates the temporary retention of a solution which can be transferred to the teeth and the surrounding soft tissue of a person's mouth.

* * * * *